United States Patent [19]

Kuramoto et al.

[11] Patent Number: 5,630,795
[45] Date of Patent: May 20, 1997

[54] CLEANING TUBE APPARATUS FOR ENDOSCOPE

[75] Inventors: Seiji Kuramoto; Ryoji Masubuchi, both of Hachioji; Akio Nakada, Fujino-machi; Yasuhiko Omagari, Hamura-machi; Ichiro Nakamura, Kokubunji; Nobuhiko Washizuka, Tama; Yoshinao Ōaki, Hachioji, all of Japan

[73] Assignee: Olympus Optical Co., Ltd., Tokyo, Japan

[21] Appl. No.: 395,524

[22] Filed: Feb. 27, 1995

Related U.S. Application Data

[63] Continuation of Ser. No. 897,354, Jun. 11, 1992, abandoned.

[30] Foreign Application Priority Data

| Aug. 2, 1991 | [JP] | Japan | 3-194454 |
| Aug. 5, 1991 | [JP] | Japan | 3-195533 |
| Oct. 11, 1991 | [JP] | Japan | 3-264072 |
| Jan. 31, 1992 | [JP] | Japan | 4-016678 |
| Apr. 16, 1992 | [JP] | Japan | 4-096473 |
| May 13, 1992 | [JP] | Japan | 4-120823 |
| May 13, 1992 | [JP] | Japan | 4-120824 |

[51] Int. Cl.⁶ .................................................. A61M 1/00
[52] U.S. Cl. .............. 604/30; 604/35; 600/157; 600/153; 600/156
[58] Field of Search ............... 128/4, 6; 604/35, 604/40, 30, 120, 275, 268, 267, 280; 600/157, 153, 156

[56] References Cited

U.S. PATENT DOCUMENTS

| 3,109,426 | 11/1963 | Noonan et al. | 604/33 |
| 3,903,877 | 9/1975 | Terada . | |
| 4,204,528 | 5/1980 | Termanini . | |
| 4,281,646 | 8/1981 | Kinoshita | 128/6 |
| 4,294,251 | 10/1981 | Greenwald et al. | 604/35 |
| 4,451,257 | 5/1984 | Atchley | 604/33 |
| 4,509,507 | 4/1985 | Yabe . | |
| 4,567,880 | 2/1986 | Goodman . | |
| 4,648,386 | 3/1987 | Morritt et al. | 604/35 |
| 4,667,656 | 5/1987 | Yabe | 604/93 |
| 4,755,168 | 7/1988 | Romanelli | 604/31 |
| 4,767,404 | 8/1988 | Renton | 604/268 |
| 4,860,731 | 8/1989 | Matsuura . | |
| 4,878,893 | 11/1989 | Chin . | |
| 4,919,113 | 4/1990 | Sakamoto et al. | 128/4 A |
| 4,991,565 | 2/1991 | Takahashi et al. | 600/157 |
| 5,007,898 | 4/1991 | Rosenbluth et al. | 606/192 |
| 5,020,539 | 6/1991 | Yokoi et al. | 128/4 |
| 5,191,878 | 3/1993 | Iida et al. | 600/157 |
| 5,203,769 | 4/1993 | Clement et al. | 604/35 |

FOREIGN PATENT DOCUMENTS

| 57-187504 | 11/1982 | Japan . |
| 64-6804 | 2/1989 | Japan . |
| 1-192328 | 8/1989 | Japan . |
| 1-310638 | 12/1989 | Japan . |
| 3-272729 | 12/1991 | Japan . |

Primary Examiner—Mark Bockelman
Attorney, Agent, or Firm—Armstrong, Westerman, Hattori, McLeland & Naughton

[57] ABSTRACT

A cleaning tube apparatus for an endoscope, comprises the endoscope having an observation optical system for observing a subject part at a forward-end portion, a cleaning tube detachable with respect to said endoscope, said cleaning tube being provided with a plurality of fluid jetting openings in a peripheral direction at one end of said cleaning tube, said fluid jetting openings being provided for leading cleaning fluid at least to said observation optical system, and a fluid supply unit connected to said cleaning tube, for supplying the cleaning fluid to said cleaning tube.

10 Claims, 24 Drawing Sheets

FIG. 35(a)     FIG. 35(b)
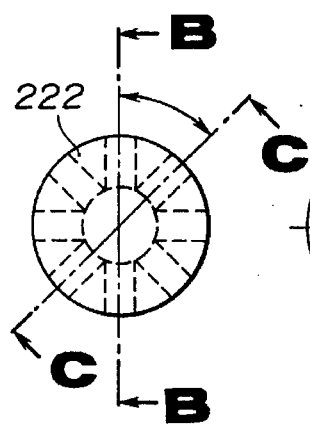 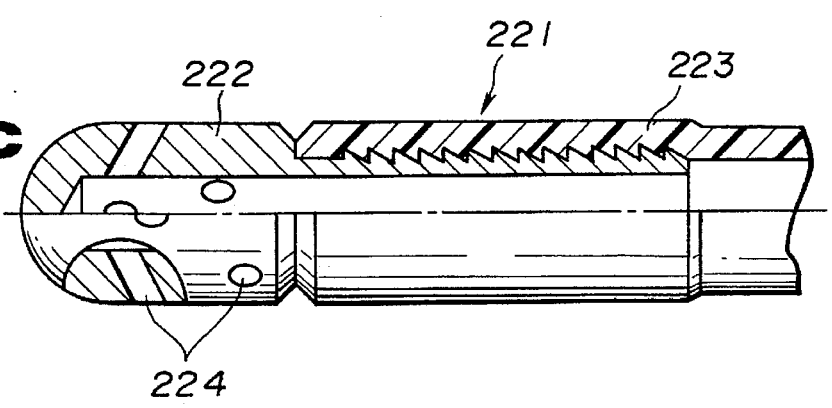
FIG. 35(c)
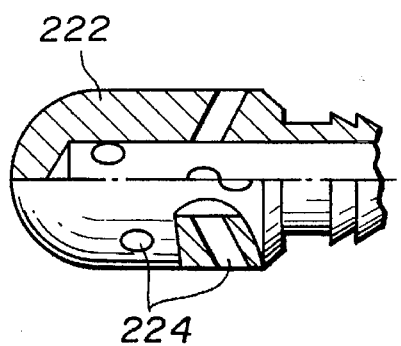

CLEANING TUBE APPARATUS FOR ENDOSCOPE

This application is a continuation of application Ser. No. 07/897,354 filed Jun. 11, 1992, now abandoned.

BACKGROUND OF THE INVENTION

1. Field of the Invention

The present invention relates to a cleaning tube apparatus for an endoscope which is provided with a cleaning tube which feeds liquid to a forward-end portion of an inserting section of the endoscope, to clean an observation optical system and the like.

2. Description of the Related Art

An endoscope, in which an elongated inserting section can be inserted into subject parts, such as a body cavity, and the like to observe and inspect the subject parts which cannot directly be viewed, and to treat the subject parts by the use of a treatment tool as occasion demands, has widely been used in a medical field of art, an industrial field of art and the like.

An endoscope apparatus is generally provided with cleaning means for cleaning objective lenses at forward-end portion of the endoscope whenever the objective lenses are so stained as to be incapable of satisfactorily executing observation, or the like.

Here, FIG. 1 of the attached drawings shows an example of an arrangement of a forward-end portion of an endoscope (for medical use, here) in an endoscope apparatus provided with cleaning means. The medical endoscope has an inserting section whose forward-end portion 52 is formed therein with an observation window 53. An objective lens system 54 is mounted on the observation window 53. The arrangement is such that an optical image is focused on a forward-end surface of an image guide 55 which is arranged on a focusing surface of the objective lens system 54.

A gas-feeding and liquid-feeding channel 56 is formed adjacent to the observation window 53. A cleaning nozzle 57 is mounted on a forward end of the gas-feeding and liquid-feeding channel 56. The cleaning nozzle 57 has a forward end thereof which is so arranged as to be bent to be directed or oriented toward an outer surface of the objective lens system 54 mounted on the observation window 53. The outer surface of the objective lens system 54 (observation window 53) stained by body liquid or the like can be cleaned by cleaning liquid or the like which is jetted from the nozzle 57. Further, the apparatus which cleans an objective lens by the cleaning nozzle provided adjacent to the objective lens has been disclosed in Japanese Utility Model Laid-Open No. SHO 57-187504, similarly to the above.

In the endoscope arranged as described above, however, since the nozzle 57 is bent, if the endoscope is used, filth or dirt and the like are liable to be deposited or stayed within the nozzle 57. It becomes difficult to completely remove and sterilize the dirt even by disinfection treatment due to disinfection liquid or the like, after the use. If the disinfection treatment is not perfect or complete, there may be a fear that the endoscope becomes a breeding source of various bacteria.

On the other hand, proposed in Japanese Utility Model Publication No. SHO 64-6804 is an arrangement in which a nozzle cap formed with a gas-feeding and water-feeding nozzle is detachably mounted on a forward-end portion of an endoscope, and other arrangements. By replacement of the nozzle cap to use the endoscope, it is possible to improve cleanness.

With the endoscope having the nozzle cap described above, however, there is a fear that, when gas-feeding and water-feeding pressures for cleaning are raised, the nozzle cap comes off. On the other hand, if the gas-feeding and water-feeding pressures are set low in order to prevent the nozzle cap from coming off, a problem occurs in which effective cleaning due to a sufficient hydraulic pressure cannot be executed.

Furthermore, disclosed in Japanese Patent Laid-Open No. HEI 3-272729 is an endoscope which is provided with a tube inserted in a channel and having a forward end thereof formed with a releasing bore for releasing fluid obliquely rearwardly. Also in this apparatus, cleaning fluid led into the tube is released from the releasing bore so that an objective lens can be cleaned.

With the apparatus disclosed in Japanese Patent Laid-Open No. HEI 3-272729, however, a plurality of jetting ports or openings are not peripherally provided, and there may occur a case where, if the inserting section is so operated as to be curved, the jetting openings are not oriented toward the objective lens because the cleaning tube rotates within the channel. In order to deal with this problem, means is provided for setting orientation, position and the like of the jetting openings with respect to the objective lens. This, however, causes malfunctions such that numbers of parts increase, processing steps increase and productivity is reduced, such that operability is reduced.

Moreover, as the endoscope apparatus provided with the cleaning means, there are endoscope apparatuses which are disclosed in Japanese Patent Laid-Open No. HEI 1-310638 and Japanese Patent Laid-Open No. HEI 1-192328.

In the endoscope apparatus disclosed in Japanese Patent Laid-Open No. HEI 1-310638, various lines for feeding water, for feeding gas and for sucking fluid are provided within a scope, and have respective rearward ends thereof which are connected to a water-feeding suction unit. Further, the endoscope apparatus has a control section which is operated in water feeding, gas feeding, suction and gas feeding in order with respect to an optical element at the forward end of the scope, by a single action operation, so that it is possible to easily clean the objective lens.

In the endoscope apparatus disclosed in Japanese Patent Laid-Open No. HEI 1-192328, control means is provided which always repeats intermittently one or more operations of the gas feeding, water feeding and suction during the use of the endoscope, so that it is possible to prevent dirt from flowing back to the various lines.

With the conventional apparatuses described above, however, since the lines for water-feeding, suction and gas-feeding are provided independently, an outer diameter of the inserting section of the endoscope is enlarged or increases. Furthermore, there is a fear that the suction nozzle, the suction lines and the like are clogged by dirt. Thus, disadvantages occur in which various bacteria or the like breed so as to be brought to a unclean or dirty condition, and the like.

SUMMARY OF THE INVENTION

It is an object of the invention to provide a cleaning tube apparatus for an endoscope, in which the endoscope and a tube serving as a cleaning line are separated from each other so that the endoscope can easily be treated in cleaning and disinfection.

It is another object of the invention to provide a cleaning tube apparatus for an endoscope, in which a cleaning line can easily be taken out or removed from an endoscope body, it is possible to maintain the line and various parts of the endoscope clean, handling is simple, it is possible to ensure that an observation optical system is cleaned, and it is possible to easily ensure a superior or good field of vision.

It is a further object of the invention to provide a cleaning tube apparatus for an endoscope, in which there are produced cleaning effects or advantages of an observation window without particular provision of guide means for leading cleaning liquid to an observation window and, accordingly, the cleaning tube apparatus can also be applied to existing endoscopes, and cleaning lines and various parts of the endoscope can be maintained clean.

It is a still further object of the invention to provide a cleaning tube apparatus for an endoscope, in which, even in case where an amount of curvature of an inserting section of the endoscope changes or torsion occurs, it is unnecessary to set a position and an orientation of a plurality of jetting openings each time, handling is easy and simple, it is possible to simply arrange the apparatus, and, even in case where the amount of curvature or the like changes, it is possible to ensure that an observation optical system is cleaned.

It is a still another object of the invention to provide a cleaning tube apparatus for an endoscope, in which it is unnecessary that lines, mechanisms and the like for cleaning are particularly provided at an inserting section of the endoscope, an outer diameter of the inserting section of the endoscope can be reduced, it is possible to ensure that an observation window is cleaned, and the endoscope can easily be treated in disinfection.

It is an object of the invention to provide a cleaning tube apparatus for an endoscope, in which it is possible to prevent danger of coming-off or falling-off of a nozzle and the like from occurring at cleaning.

According to the invention, there is provided a cleaning tube apparatus for an endoscope, comprising:

the endoscope having an observation optical system for observing a subject part at a forward-end portion;

a cleaning tube detachable with respect to the endoscope, the cleaning tube being provided with a plurality of fluid jetting openings in a peripheral direction at one end of the cleaning tube, the fluid jetting openings being provided for leading cleaning fluid at least to the observation optical system; and fluid supply means connected to the cleaning tube, for supplying the cleaning fluid to the cleaning tube.

BRIEF DESCRIPTION OF THE DRAWINGS

FIGS. 2 to 6 are views showing a first embodiment of the invention, FIG. 2 being a view for explanation, showing an entire arrangement of a cleaning tube apparatus;

FIG. 3 is a perspective view showing an arrangement of a forward end of a cleaning tube;

FIG. 4 is a block diagram showing an arrangement of a liquid-feeding suction unit;

FIG. 5 is a view for explanation, explaining operation of the liquid-feeding suction unit;

FIG. 8 is a block diagram showing an arrangement of a water-feeding suction unit;

FIG. 10 is a cross-sectional view for explanation, showing an arrangement of a flow-passage switching portion;

FIG. 11 is a cross-sectional view for explanation, showing an arrangement of a modification of the flow-passage switching portion;

FIG. 18 is a view for explanation, showing an entire apparatus under a condition that the cleaning catheter is mounted;

FIG. 20 is a cross-sectional view showing a forward-end portion of an endoscope under a condition that the cleaning catheter according to the eighth embodiment is mounted;

FIG. 22 is a cross-sectional view showing a forward-end portion of an endoscope under a condition that the cleaning catheter according to the ninth embodiment is mounted;

FIG. 25 is a view for explanation, showing an arrangement of an entire cleaning tube apparatus;

FIG. 26 is a cross-sectional view taken along a line A—A in FIG. 24;

FIG. 27 is a view for explanation, showing an arrangement of a forward-end portion of a cleaning catheter;

FIG. 28 is a view for explanation, showing an arrangement of a positioning mechanism for the cleaning catheter;

FIG. 29 is a view for explanation, showing a condition under which the positioning mechanism is loosened or unfastened;

FIG. 30 is a view for explanation, showing a condition under which the positioning mechanism is tightened;

FIG. 32 is a view for explanation, showing an arrangement of a forward-end portion of a cleaning tube;

FIG. 33 is a view for explanation, showing a condition under which the cleaning tube is inserted into a channel in an endoscope so as to be operated in curvature;

FIG. 34 is a view for explanation, showing operation at the time the cleaning tube is inserted into the channel in the endoscope so as to be operated in curvature;

FIGS. 35(a), 35(b) and 35(c) to 37 are views showing a thirteenth embodiment of the invention, FIGS. 35(a), 35(b) and 35(c) being views showing an arrangement of a forward-end portion of a cleaning tube, FIG. 35(a) being a front elevational view as viewed from a forward end of the cleaning tube, FIG. 35(b) being a partially broken-away or cut-away cross-sectional view taken along a line B—B in FIG. 35(a), FIG. 35(c) being a partially cut-away cross-sectional view taken along a line C—C in FIG. 35(a);

FIG. 36 is a partially cut-away cross-sectional view showing an arrangement of a fixing portion of the cleaning tube;

FIG. 37 is a view for explanation, showing a condition under which the fixing portion of the cleaning tube is fixed to an opening of a channel in the endoscope;

FIG. 40 is a view for explanation, showing an arrangement of an entire cleaning tube apparatus;

FIGS. 43(a) and 43(b) are perspective views showing an arrangement of a forward-end portion of a cleaning tube apparatus;

FIG. 48 is a view for explanation, showing a condition under which an endoscope is inserted.

DETAILED DESCRIPTION OF THE PREFERRED EMBODIMENTS

Referring first to FIGS. 2 through 6, there is shown a first embodiment of the invention.

Figure 1:
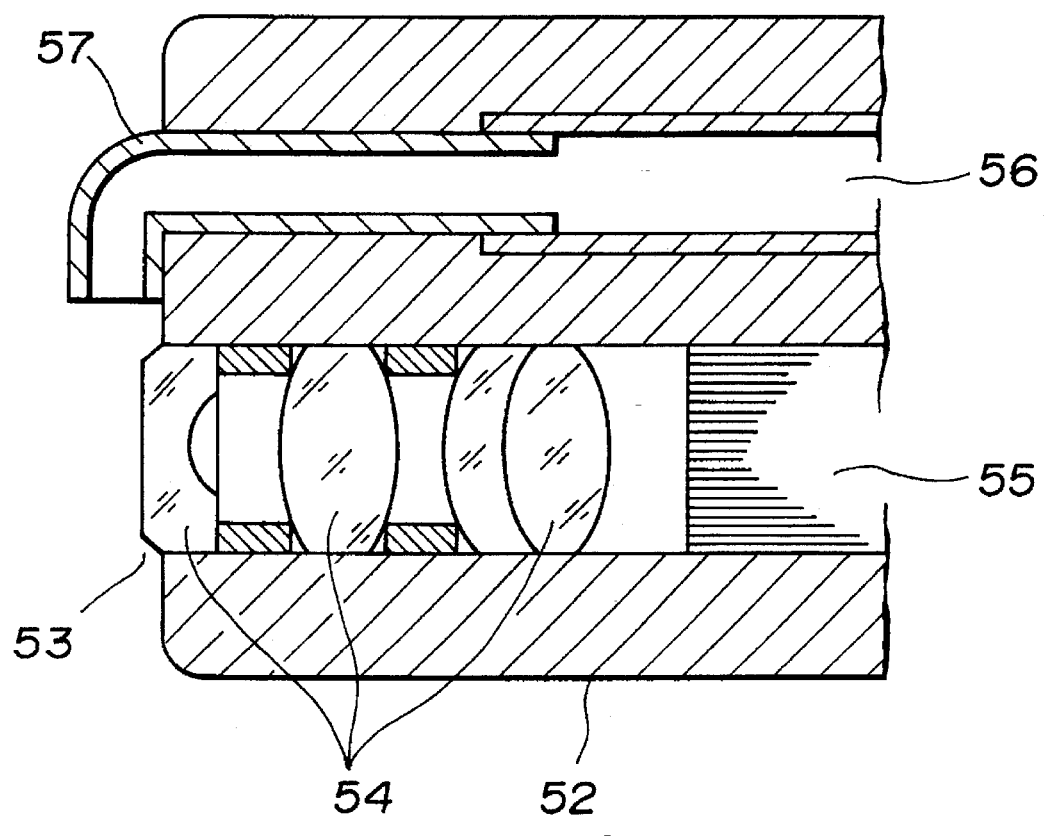
FIG. 1 is a cross-sectional view showing an example of an arrangement of a forward-end portion of a conventional endoscope.
Figure 2:
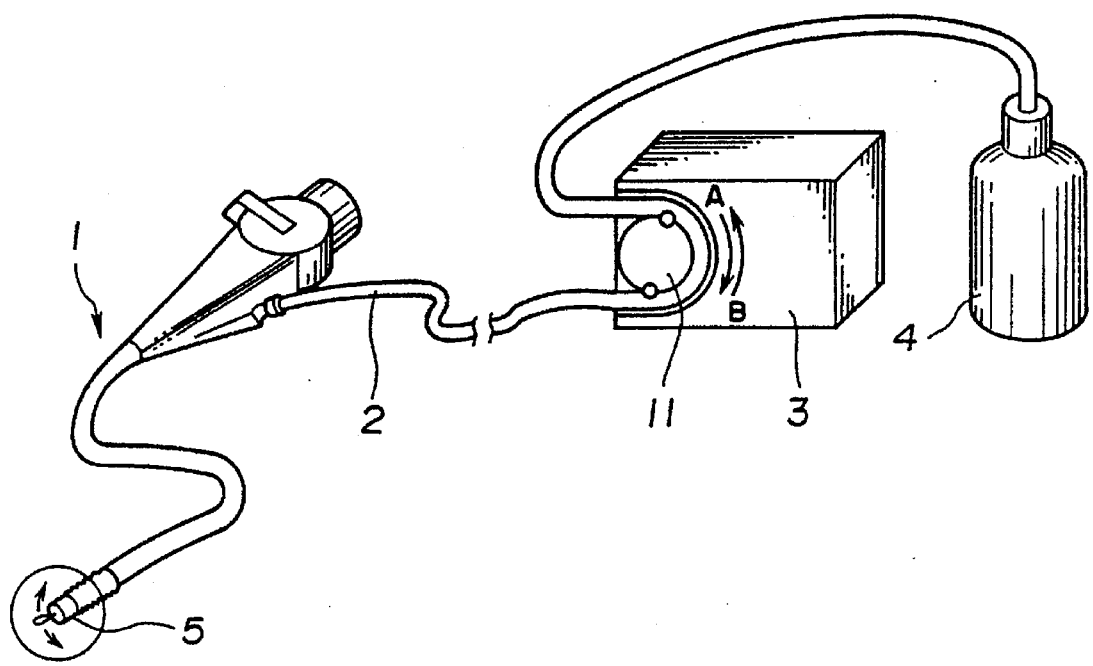

As shown in FIG. 2, a cleaning tube apparatus according to the present embodiment is so arranged as to comprise a cleaning tube 2 insertable and retractable with respect to a treatment-tool channel in an endoscope 1, a liquid-feeding suction unit 3 serving as fluid supply means for feeding and sucking cleaning fluid, for example, cleaning liquid with respect to the cleaning tube 2, and a liquid supply tank 4.

Figure 3:
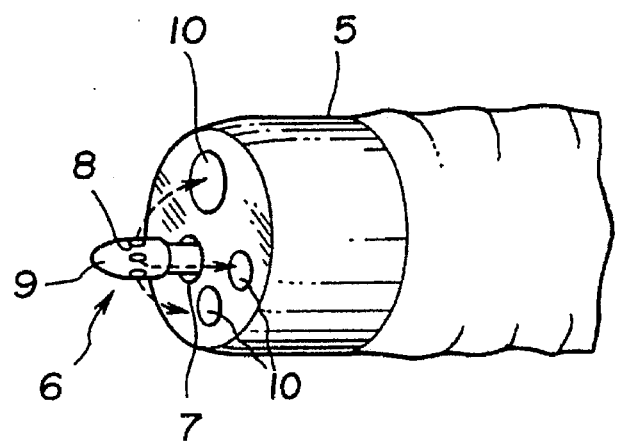

FIG. 3 is an enlarged view showing an arrangement of a forward-end portion 5 of the endoscope 1. The cleaning tube 2 is inserted through the treatment-tool channel in the endoscope 1 and has a forward-end portion 6 which projects from a channel opening 7. At the forward-end portion 6, a forward-end tip 9 is provided which has a plurality of cleaning-liquid jetting ports or openings 8. The arrangement is such that the cleaning liquid is jetted from the cleaning-liquid jetting openings 8 to clean objective lenses 10.

The liquid-feeding suction unit 3 is provided with a rotary pump 11. The arrangement is such that, when the rotary pump 11 rotates in a direction A in FIG. 2, the cleaning liquid within the liquid supply tank 4 is sent or fed to the cleaning tube 2 to clean the objective lenses 10, while, when the rotary pump 11 rotates in a direction B, the cleaning liquid is sucked toward the liquid supply tank 4 so that water drops remaining on the objective lenses 10 are sucked.

Figure 4:
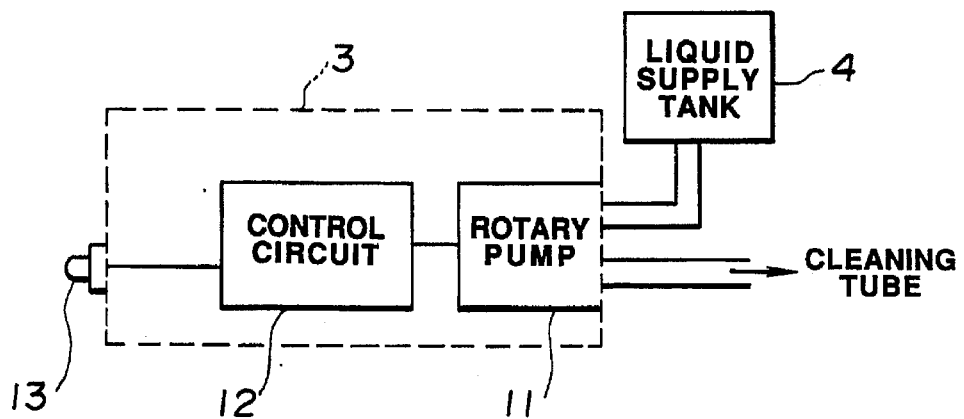

As shown in FIG. 4, the rotary pump 11 is arranged such that the rotary pump 11 is connected to a control circuit 12 arranged within the liquid-feeding suction unit 3, and operation of the rotary pump 11 is controlled by the control circuit 12. A start switch 13 for indicating start of cleaning and suction operations is connected to the control circuit 12.

Operation of the present embodiment will next be described.

Figure 5:
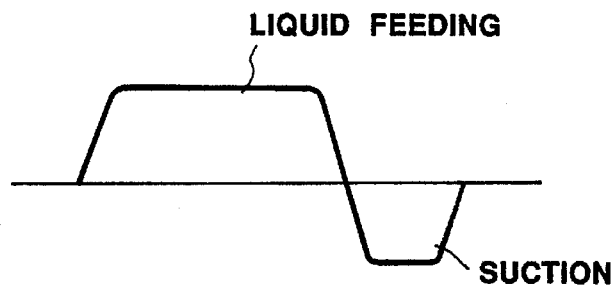

When the start switch 13 is depressed, the liquid-feeding suction unit 3 feeds the liquid for a predetermined period of time, as shown in FIG. 5, and, subsequently, executes suction for a short period of time. Specifically, the rotary pump 11 rotates for the predetermined period of time in the direction A in FIG. 2 on the basis of an operating condition set beforehand in the control circuit 12 and, subsequently, the rotary pump 11 rotates for the short period of time in the direction B to feed the liquid and to suck the same.

First, the cleaning liquid is fed to the cleaning tube 2 from the liquid supply tank 4, by the rotary pump 11, and is fed to the forward-end portion 6 through the cleaning tube 2. As shown in FIG. 3, the cleaning liquid fed to the forward-end portion 6 of the cleaning tube 2 is jetted toward the objective lenses 10 from the plurality of the cleaning-liquid jetting openings 8 in the forward-end tip 9, to clean the objective lenses 10.

Figure 6A:
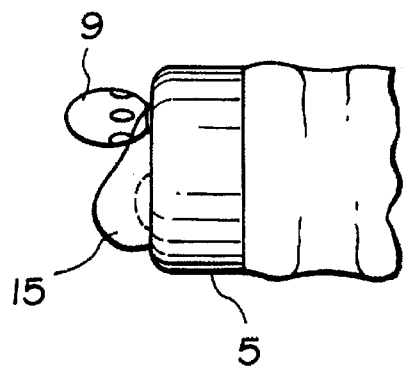
FIGS. 6(a) and 6(b) are views for explanation, showing a condition of the forward end of the cleaning tube at suction.
Figure 6B:
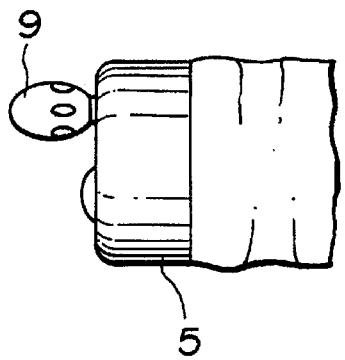

Cleaning has been executed for the predetermined period of time and, subsequently, the rotary pump 11 rotates in a reverse direction to execute suction. As shown in FIG. 6(a), there is a case where, after cleaning, a water drop 15 remains on the objective lenses 10 to prevent or disturb a field of view. In view of this case, the water drop 15 is sucked through the cleaning-liquid jetting openings 8 in the forward-end tip 9, whereby, as shown in FIG. 6(b), the water drop 15 is removed so that the field of vision can superiorly be secured or ensured.

Since, at liquid feeding and suction, the cleaning tube 2 is inserted into the treatment-tool channel, there is no case where filth or dirt or the like enters the channel. Further, by pulling-out of the cleaning tube 2, it is possible to ensure that the cleaning tube 2 and an interior of the treatment-tool channel in the endoscope are easily disinfected.

As described above, according to the present embodiment, since the cleaning tube insertable and extractable with respect to the treatment-tool channel in the endoscope is provided to clean the objective lenses, the cleaning tube can easily be pulled out from the endoscope to clean and disinfect the cleaning tube. There is also no case where dirt is lodged in the interior of the endoscope, and cleaning of the interior of the channel can easily be executed. Thus, it is possible to maintain various parts clean. Specifically, it is possible to simplify handling of the apparatus at cleaning and disinfection, and it is possible to ensure cleaning and disinfection treatments. Furthermore, since liquid feeding and suction are executed only by a single cleaning tube, a single line is sufficient, and it is possible to reduce the diameter of the inserting section of the endoscope. Moreover, since the cleaning liquid is jetted toward the objective lenses, and the water drop remaining on the objective lenses is sucked after the cleaning operation, it is possible to ensure that the objective lenses are cleaned, and it is possible to ensure a superior field of vision immediately after the cleaning.

Figure 7:
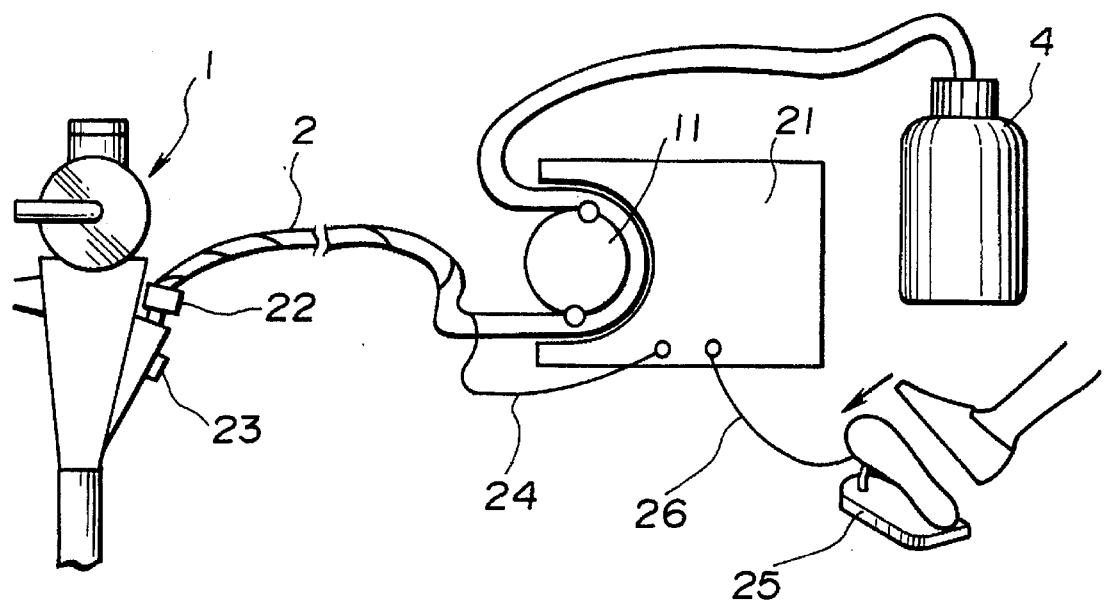
FIGS. 7 and 8 are views showing a second embodiment of the invention, FIG. 7 being a view for explanation, showing an arrangement of a cleaning tube apparatus.
Figure 8:
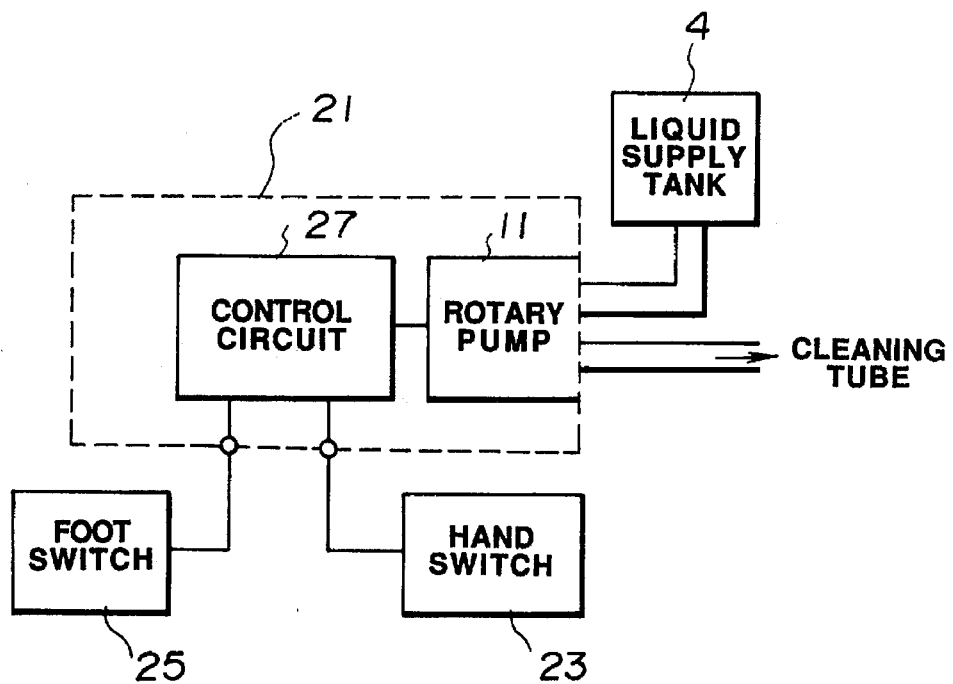

FIGS. 7 and 8 show a second embodiment of the invention. FIG. 7 is a view for explanation, showing an arrangement of a cleaning tube apparatus, while FIG. 8 is a block diagram showing an arrangement of a liquid-feeding suction unit.

The second embodiment is an example in which a switch capable of executing operations such as liquid feeding and suction at a hand is provided in addition to the arrangement of the first embodiment. Arrangements of a cleaning tube 2, a rotary pump 11 and the like are similar to those of the first embodiment.

As shown in FIG. 7, a hand switch 23 for indicating operation of a liquid-feeding suction unit 21 is provided at an endoscope operating section adjacent to a treatment-tool channel opening 22 into which the cleaning tube 2 is inserted. The hand switch 23 is connected to the liquid-feeding suction unit 21 through a signal line 24. Further, a foot switch 25 is provided which is capable of executing indication similar to that of the hand switch 23. The foot switch 25 is connected to the liquid-feeding suction unit 21 through a signal line 26.

As shown in FIG. 8, the liquid-feeding suction unit 21 is provided with a control circuit 27 for controlling operation of the rotary pump 11. Connected to the control circuit 27 are the rotary pump 11, the hand switch 23 and the foot switch 25. Specifically, rotation of the rotary pump 11 is controlled in accordance with indication from the hand switch 23 or the foot switch 25, to feed and suck the liquid with respect to the cleaning tube 2.

In the embodiment, the hand switch 23 or the foot switch 25 is turned ON/OFF, whereby operation (feeding and suction of the liquid) of the rotary pump 11 is controlled. For example, in case where any one of the hand switch 23 and the foot switch 25 is turned ON, the liquid-feeding operation is executed to feed the cleaning liquid within a liquid supply tank 4 to the cleaning tube 2, thereby cleaning objective lenses. Subsequently, when the switch is turned OFF, the suction operation is executed for a predetermined period of time, to suck water drops remaining on the objective lenses. Alternatively, the arrangement may be such that operations of liquid-feeding, suction and stopping are switched each time the switch is depressed.

In this manner, in the second embodiment, operations of liquid-feeding and suction can be executed by the hand switch 23 and the foot switch 25. Accordingly, in case where there is dirt, difficult to be removed, on the objective lenses, and the like, it is possible to execute liquid-feeding and suction, not for a predetermined period of time, but until sufficient cleaning is completed. Furthermore, it is possible to easily execute operations of liquid-feeding and suction of the cleaning liquid, by an operator at hand or at foot.

Other operation and advantages are similar to those of the first embodiment.

Figure 9:
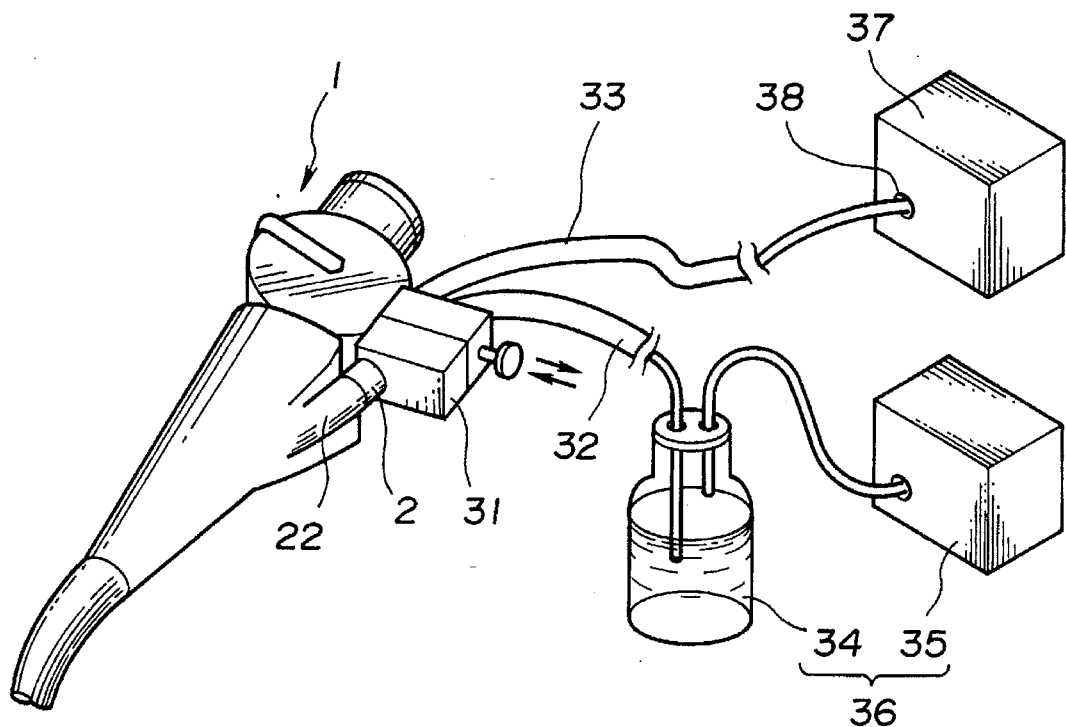
FIGS. 9 to 11 are views showing a third embodiment of the invention, FIG. 9 being a view for explanation, showing an arrangement of a cleaning tube apparatus.
Figure 10:
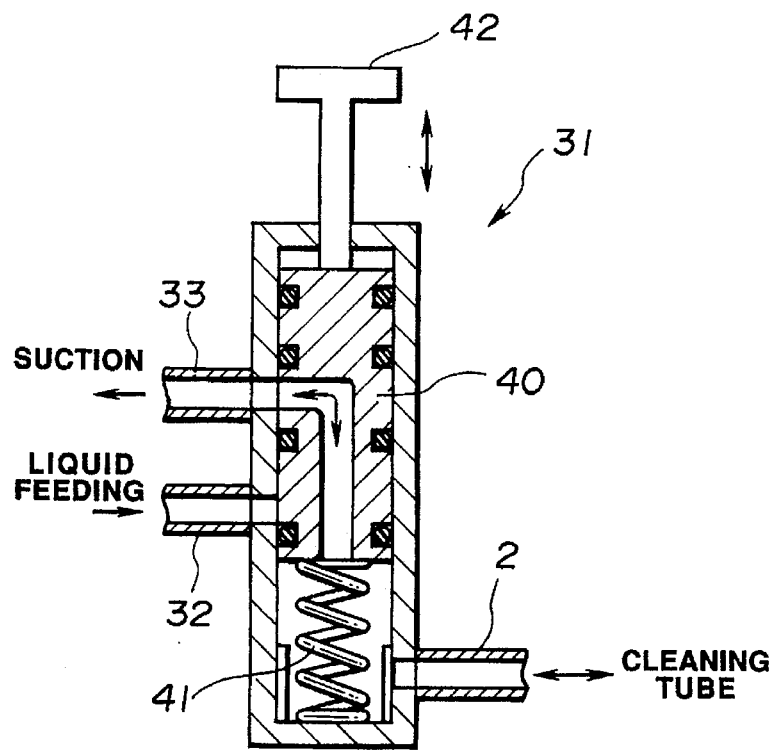
Figure 11:
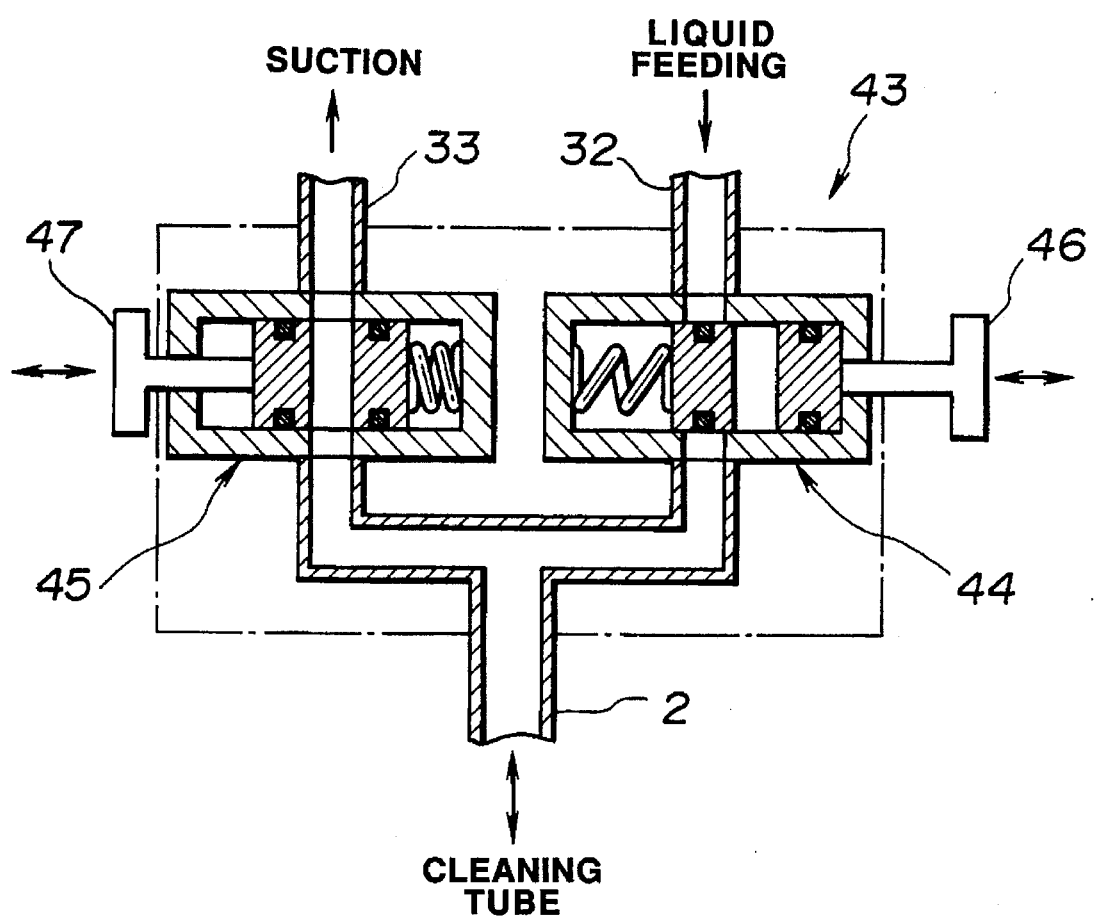

FIGS. 9 to 11 show a third embodiment of the invention. FIG. 9 is a view for explanation, showing an arrangement of a cleaning tube apparatus, and FIG. 10 is a cross-sectional view for explanation, showing an arrangement of a flow-passage switching portion, while FIG. 11 is a cross-sectional view for explanation, showing an arrangement of a modification of the flow-passage switching portion.

As shown in FIG. 9, in the third embodiment, a cleaning tube 2, which is inserted from a treatment-tool channel opening 22 in an endoscope 1, is provided with a flow-passage switching section 31 at a hand, and branches off into a liquid feeding tube 32 and a suction tube 33 by the passage switching section 31. An aquapurator 36 having a liquid supply bottle 34 and a pump 35 is connected to a portion of the liquid feeding tube 32 adjacent to a rearward end thereof. Further, a suction unit 37 having a suction pump and the like has a suction opening 38 which is connected to a portion of the suction tube 33 adjacent to a rearward end thereof.

As shown in FIG. 10, the flow-passage switching section 31 is arranged such that a valve 40 is provided within a cylinder, and is biased by a spring 41. A flow-passage operating portion 42 provided in extension on the valve 40 is depressed to advance and retreat the valve 40, whereby a flow passage from the cleaning tube 2 is switched so that operations of liquid-feeding and suction can be switched.

A modification of the flow-passage switching section is illustrated in FIG. 11. A flow-passage switching section 43 in this modification is arranged such that a pair of valves 44 and 45 are provided respectively in a liquid-feeding flow passage and a suction flow passage. Flow-passage operating portions 46 and 47 provided in extension respectively on the valves are depressed to advance and retreat the valves 44 and 45, whereby the flow passage from the cleaning tube 2 is switched to switch operations of liquid feeding and suction.

Other arrangements of the cleaning tube 2 and the like are similar to those of the first embodiment.

The cleaning liquid is fed to the flow-passage switching section 31 through a liquid-feeding tube 32 by the aquapurator 36. Further, suction is executed by a suction tube 33 by the suction unit 37. Here, in case where the flow-passage switching section 31 is operated to cause the liquid-feeding tube 32 and the cleaning tube 2 to communicate with each other so that, in case where a condition is brought to a liquid-feeding condition, the cleaning liquid is fed to the cleaning tube 2 and is fed to a forward-end portion 6 to clean the objective lenses. After completion of the cleaning, when the operating portion 42 of the flow-passage switching section 31 is operated to switch the flow passage to cause the suction tube 33 and the cleaning tube 2 to communicate with each other so that a condition is brought to a suction condition, the cleaning liquid within the cleaning tube 2 is sucked toward the suction opening 38, by the suction unit 27, so that water drops remaining on the objective lenses are sucked.

In this manner, also in the present embodiment, similarly to the first embodiment, it is possible to easily pull out the cleaning tube from the endoscope to clean and disinfect the same, and it is possible to maintain various lines clean. On the other hand, it is possible to ensure that the objective lenses are cleaned, and it is possible to easily ensure a superior or good field of view.

A modification of the gas feeding line, the liquid feeding line and the suction line together with a gas feeding, liquid feeding and suction unit connected thereto will next be described.

Figure 12:
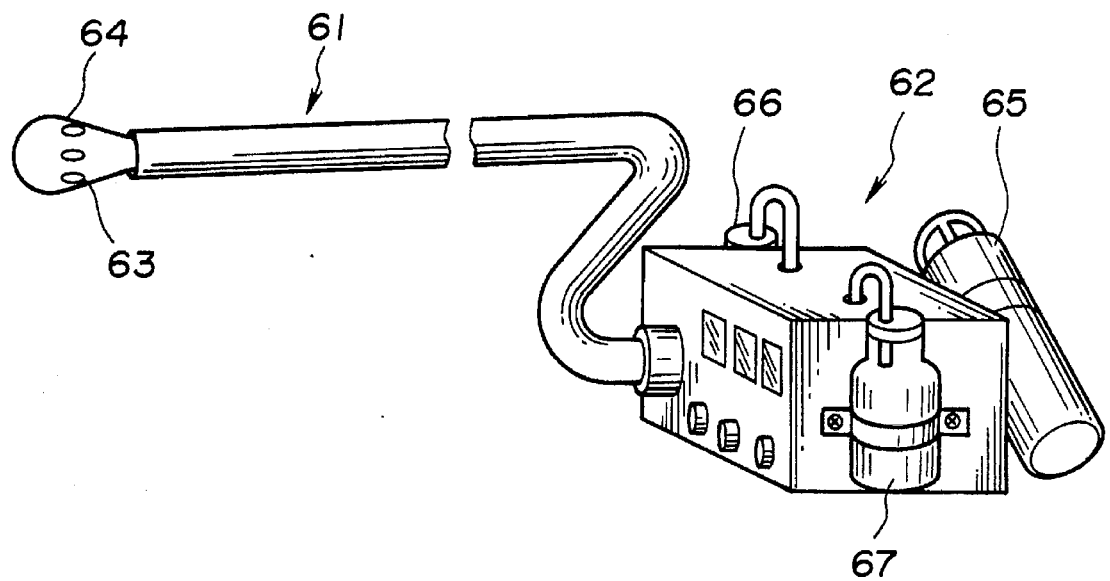
FIG. 12 is a view for explanation, showing an arrangement of a cleaning tube apparatus according to a fourth embodiment of the invention.

FIG. 12 is a view for explanation, showing an arrangement of a cleaning tube apparatus according to a fourth embodiment of the invention.

The cleaning tube apparatus according to the fourth embodiment is arranged such that a cleaning-liquid supply unit 62 having gas feeding means, liquid feeding means and suction means is connected to a tube 61 which leads cleaning fluid.

A forward-end tip 64 having a plurality of jetting openings 63 is provided at the forward-end portion of the tube 61, so that cleaning liquid and gas supplied from the cleaning-liquid supply unit 62 are outgone or sucked in a predetermined direction through the tube 61. The cleaning-liquid supply unit 62 is provided with a gas feeding bomb 65 of the gas feeding means, a liquid feeding tank 66 of the liquid feeding means and a suction tank 67 of the suction means. Supply and suction of the cleaning liquid or the cleaning gas are executed by a selector valve, a pump or the like (not shown) which is arranged on the inside of the cleaning-liquid supply unit 62.

When an endoscope is used, similarly to the first embodiment, the tube 61 is inserted through a channel in the endoscope, and is fixed under a condition that the forward-end tip 64 projects from a forward end of the inserting section of the endoscope. The cleaning liquid is fed out by the cleaning-liquid supply unit 62, and is led to the forward-end tip 64 through the tube 61. Then, the cleaning liquid is expelled in a predetermined direction from the plurality of jetting openings 63 in the forward-end tip 64, so that forward-end portion of the endoscope is cleaned. Subsequently, the gas is fed out by the cleaning-liquid supply unit 62, and is jetted from the jetting openings 63 through the tube 61 such that water drops remaining on the forward end of the endoscope are blown off. Further, in case where there are remaining water drops, suction is executed by the jetting openings 63 in the forward-end tip 64 by the cleaning-liquid supply unit 62 to remove the water drops.

In this manner, the tube connected to the cleaning-liquid supply unit is detachably inserted in the channel in the endoscope, whereby, similarly to the first embodiment, the fourth embodiment has function capable of cleaning the forward-end portion of the endoscope. It is possible to easily separate the endoscope and the tube from each other to clean and disinfect the endoscope and the tube separately from each other. Thus, it is possible to maintain various parts and portions clean. Furthermore, it is possible for the embodiment to execute gas feeding, liquid feeding and suction by a simple arrangement comprising only a single tube.

Figure 13:
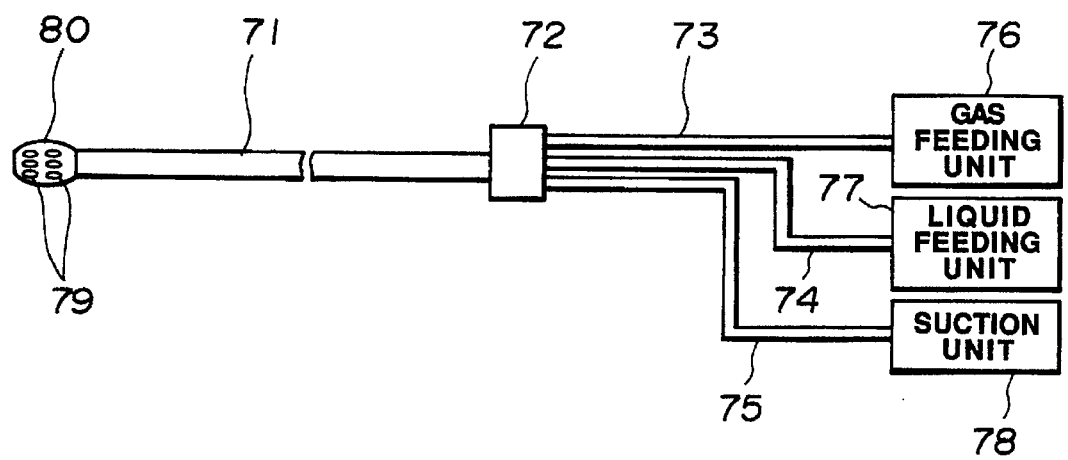
FIG. 13 is a view for explanation, showing an arrangement of a cleaning tube apparatus according to a fifth embodiment of the invention.

FIG. 13 is a view for explanation, showing an arrangement of a cleaning tube apparatus according to a fifth embodiment of the invention.

In the fifth embodiment, a first tube 71 is provided which has therein a single lumen. Three second tubes 73, 74 and 75 are detachably connected to the first tube 71 through a connecting portion 72 which serves also as a holding portion connected to a proximal-end portion of the first tube 71. Check valves are arranged within the connecting portion 72 every second tubes 73, 74 and 75, respectively. A gas feeding unit 76, a liquid feeding unit 77 and a suction unit 78 are connected respectively to these second tubes 73, 74 and 75, so that supply or suction of the fluid is executed. The first tube 71 has a forward-end portion thereof Which is provided with a forward-end tip 80 formed with a plurality of jetting openings 79 in two rows.

In the present embodiment, the first tube 71 is inserted into a channel in an endoscope, the forward-end tip 80 projects from a forward end of an inserting section of the endoscope, and gas or liquid is fed out by the gas feeding unit 76 and the liquid feeding unit 77. The cleaning gas or liquid fed out is led to the forward-end tip 80 of the tube, and is outgone from the plurality of jetting openings 79 in the forward-end tip 80, so that the forward-end portion of the endoscope is cleaned. Moreover, suction is executed by the suction unit 78 through the forward-end tip 80 and the first tube 71. At this time, by the check valves provided within the connecting portion 72, the liquid sucked does not flow back toward the second tubes 73 and 74 which are connected to the gas feeding unit 76 and the liquid feeding unit 77.

In this manner, the arrangement executing liquid feeding, gas feeding and suction through the three tubes branching on the way has also function capable of cleaning the forward-end portion of the endoscope, similarly to the fifth embodiment. Further, it is possible for the above-described arrangement to easily separate the endoscope and the tube from each other, to clean and disinfect the endoscope and the tube separately from each other. Thus, it is possible to keep various parts and portions clean. Furthermore, since the tube branches on the way into exclusive lines, flowing-back, clogging and the like can be prevented from occurring. Thus, it is possible to maintain the lines clean.

Figure 14:
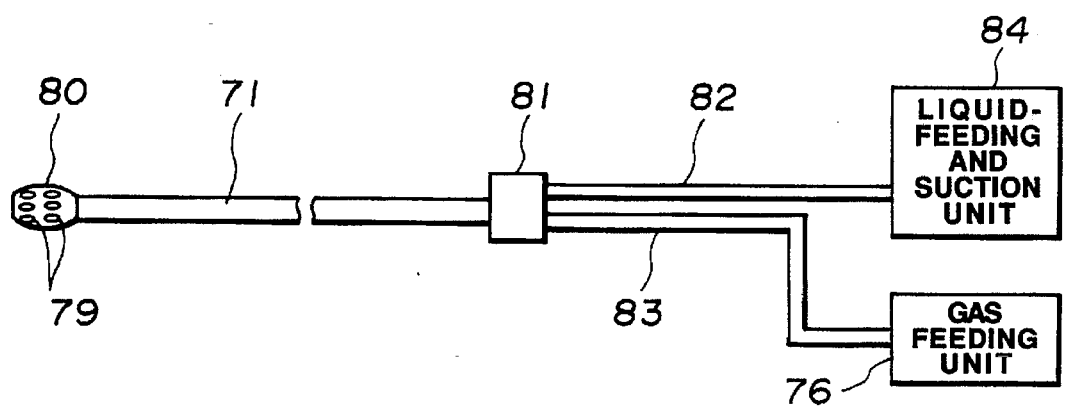
FIG. 14 is a view for explanation, showing an arrangement of a modification of the fifth embodiment.

FIG. 14 shows an arrangement of a modification of the fifth embodiment.

In the modification, two second tubes 82 and 83 are detachably connected through a connecting portion 81 which is connected to a proximal-end portion of a first tube 71. A liquid feeding and suction unit 84 and a gas feeding unit 76, which have liquid feeding suction and suction function, are connected respectively to the second tubes 82 and 83. Others are arranged similarly to those of the fifth embodiment.

In this manner, even in case where liquid feeding and suction are executed on one hand, and gas feeding is executed on the other hand, through the two tubes branching on the way, there are produced function and advantages similar to those of the fifth embodiment.

Figure 15:
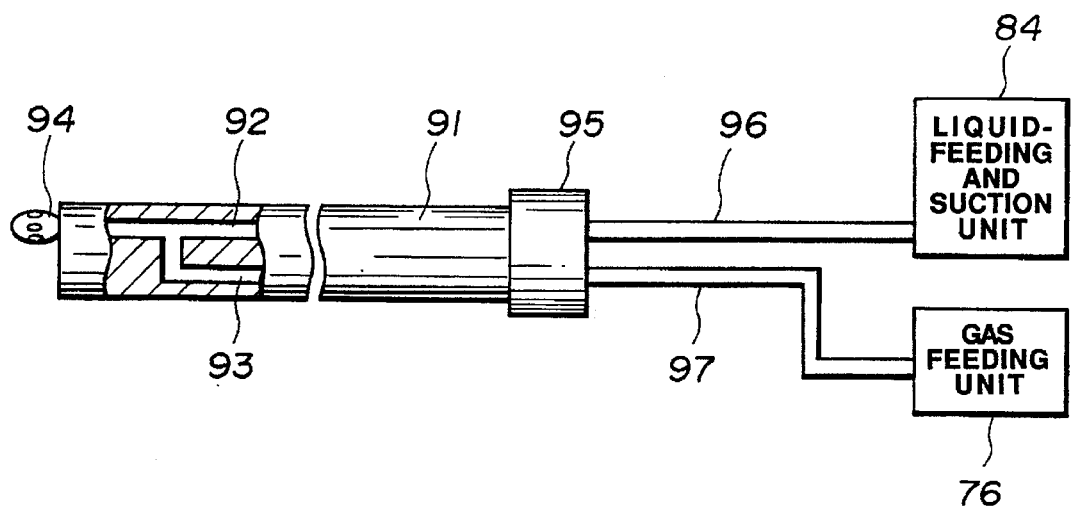
FIG. 15 is a view for explanation, showing an arrangement of a cleaning tube apparatus according to a sixth embodiment of the invention.

FIG. 15 is a view for explanation, showing an arrangement of a cleaning tube apparatus according to a sixth embodiment of the invention.

The cleaning tube apparatus according to the sixth embodiment is provided with a first tube 91 which is provided with a plurality of lumens (two, here) 92 and 93. The two lumens 92 and 93 are joined together at a forward end of the first tube 91, and communicate with a forward-end tip 94. The first tube 91 has a proximal-end portion thereof which is provided with a connecting portion 95 serving also as a holding portion. Two second tubes 96 and 97 are detachably connected through the connecting portion 95. A liquid feeding and suction unit 84 and a gas feeding unit 76 are connected respectively to the second tubes 96 and 97. Others are arranged similarly to the fifth embodiment, and the description thereof will be omitted.

In this manner, the arrangement, in which a tube is provided which has a plurality of lumens, and liquid feeding, suction and gas feeding are executed by lines which are separated from each other to the forward-end portion of the tube, has function capable of cleaning the forward-end portion of the endoscope similarly to the fifth embodiment. It is possible to easily separate the endoscope and the tube from each other to clean and disinfect the endoscope and the tube separately from each other. Thus, it is possible to maintain various parts and portions clean. Moreover, since the lines for liquid feeding and drawing and for gas feeding are separately provided on the tube, it is possible to ensure that liquid feeding and gas feeding are executed.

Figure 16:
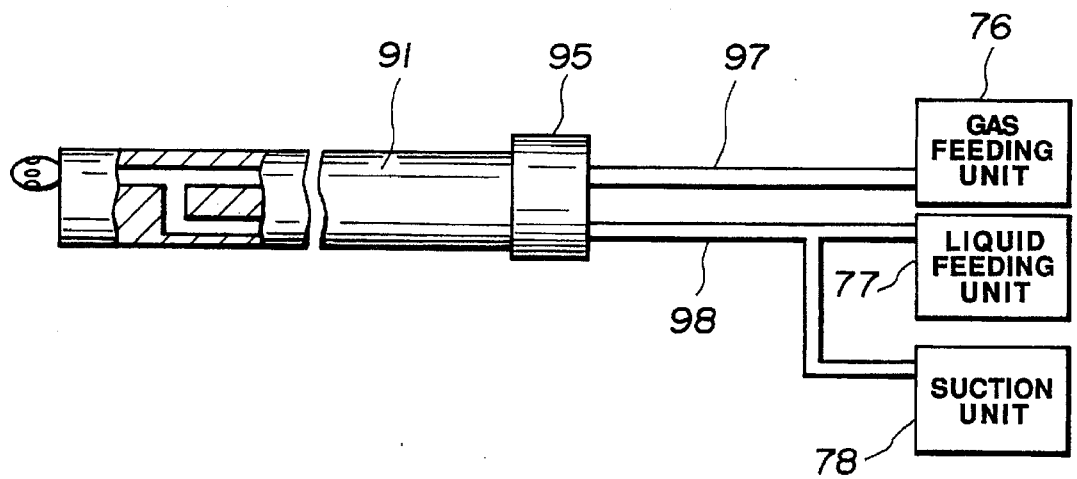
FIG. 16 is a view for explanation, showing an arrangement of a modification of the sixth embodiment of the invention.

FIG. 16 shows an arrangement of a modification of the sixth embodiment.

The modification is arranged such that a separate gas feeding unit 76, a separate liquid feeding unit 77 and a separate suction unit 78 are connected to a first tube 91 having a plurality of lumens. Two second tubes 97 and 98 are connected to the first tube 91 through a connecting portion 95. However, the gas feeding unit 76 is connected to one of the tubes 97, while the other tube 98 branches into two pipe portions on the way so that the liquid feeding unit 77 and the suction unit 78 are connected respectively to the two branching pipe portions. Others are arranged similarly to the sixth embodiment.

In this manner, the arrangement in which the tube having the plurality of lumens is provided, and the separate gas feeding unit, the separate liquid feeding unit and the separate suction unit are connected to the tube to execute liquid feeding, suction and gas feeding has also function capable of cleaning the forward-end portion of the endoscope similarly to the fifth embodiment and the sixth embodiment, and it is possible to easily clean and disinfect various parts and portions.

A modification of the cleaning tube will next be described with reference to seventh and subsequent embodiments.

Figure 17:
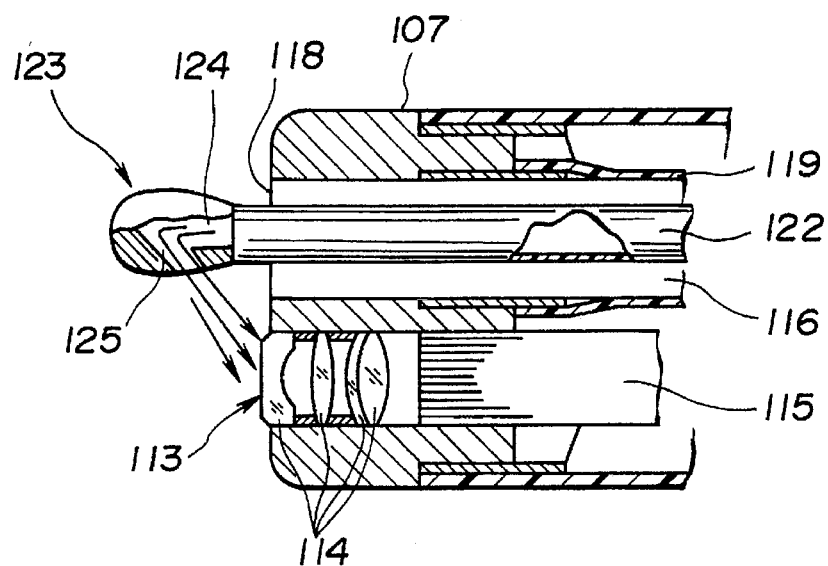
FIGS. 17 and 18 are views showing a seventh embodiment of the invention, FIG. 17 being a cross-sectional view showing a forward-end portion of an endoscope under a condition that a cleaning catheter according to the seventh embodiment is mounted.
Figure 18:
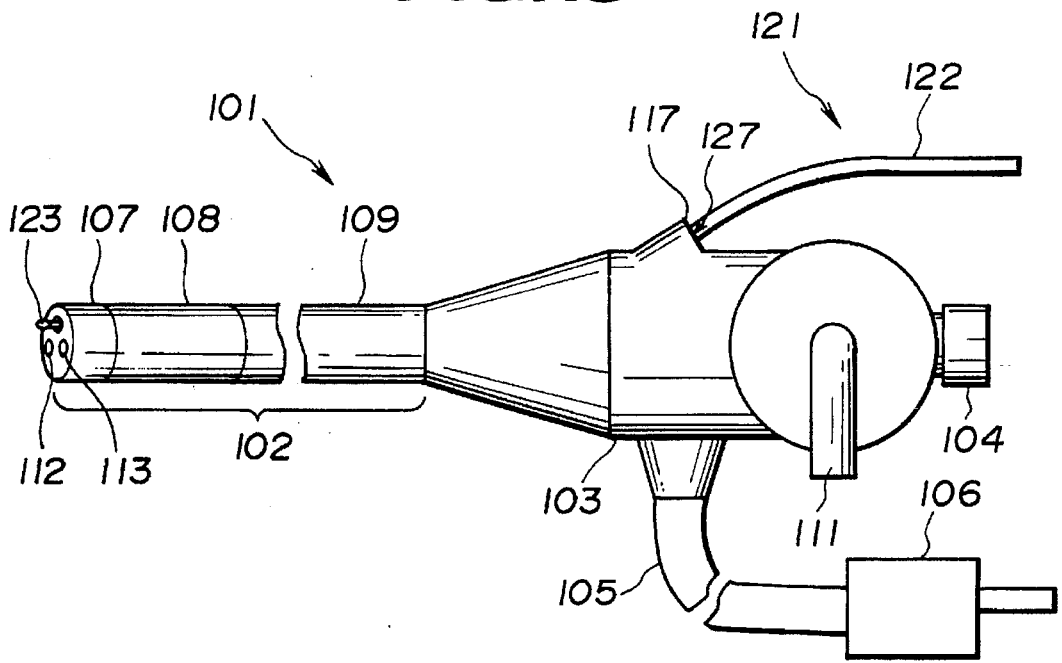

FIGS. 17 and 18 show the seventh embodiment of the invention.

As shown in FIG. 18, an endoscope 101 for observing an interior of a pleural cavity, for example, which is provided with a cleaning tube apparatus according to the seventh embodiment has an inserting section 102 having built therein observing means and so elongated as to be capable of being inserted into an interior of a body cavity or the like and having resiliency, elasticity or flexibility, an operating section 103 connected to a rearward end of the inserting section 102 and large in width, an ocular or eyepiece section 104 formed at a rearward end of the operating section 103, and a light guide cable 105 extending from a lateral portion of the operating section 103. The arrangement is such that a connector 106 mounted on an end of the light guide cable 105 is detachably connected to a light-source unit (not shown).

The inserting section 102 has, from a forward end thereof, a hard forward-end portion 107, a curving portion 108 capable of being curved, and a flexible tube portion 109 having flexibility. The arrangement is such that, by operation of a curving knob 111 provided at the operating section 103, the curving portion 108 is capable of being curved.

The connector 106 of the light guide cable 105 is connected to the light source unit, whereby white light of a lamp (not shown) within a light source unit is illuminated to an end face of a light guide. The illuminating light transmitted by the light guide is outgone forwardly from an illuminating window 112 which is provided in an end face of the inserting section 102 adjacent to the forward-end portion 107, to illuminate subject parts (not shown).

The subject parts illuminated by the illuminating light are arranged such that an optical image is focused on one of a pair of end faces of an image guide 115 fixed to the focusing surface, by an objective lens system 114 illustrated in FIG. 17, and provided in an observing window 113 in the forward-end portion 107. By the image guide 115, the optical image is transmitted to the other end face of the inserting section 102, adjacent to the ocular section 104. An ocular lens (not shown) is arranged opposite to the other end face of the inserting section 102, and it is possible to observe in enlargement, by the naked eye, the subject parts through the ocular lens.

The endoscope 101 is provided with a channel 116 so as to be capable of inserting therein a treatment tool or the like to execute medical treatment or the like. The channel 116 extends from an inserting opening 117 in the operating section 103 illustrated in FIG. 18, to a forward-end opening 118 (refer to FIG. 17) in the forward-end portion 107 through the inserting section 102. The channel 116 is formed by a tube 119 which is flexible within the inserting section 102. The tube 119 has a forward-end portion thereof which is secured to a base or mouthpiece fixed to a through bore in the forward-end portion 107.

A cleaning catheter 121 to be described subsequently is inserted into the channel 116 in the endoscope 101 and can serve as cleaning means for cleaning an outer surface of the observation window 113 or the like, that is, an outer surface of the objective lens system 114 and the like.

As shown in FIGS. 17 and 18, the cleaning catheter 121 has a hollow catheter body 122, and a cap 123 formed integrally on one of a pair of ends (forward end portion) of the catheter body 122. The other opening end of the catheter body 122 is detachably connected to a gas-feeding liquid-feeding suction unit (not shown), so as to be capable of leading fluid such as liquid, gas or the like supplied from the gas-feeding liquid-feeding suction unit, to the forward end of the catheter body 122.

The catheter body 122 is formed by a tube having flexibility, and has an outer diameter capable of being inserted into the channel 116. Further, in the present embodiment, the cap 123 has a configuration thereof approximate to an elliptical sphere. The cap 123 is formed with a hollow portion 124 communicating with a forward-end opening in the catheter body 122, and an outgoing path 125 communicating in an acute angle (that is, communicating in the letter of V) with a hollow flow passage in the catheter body 122 from a top of the hollow portion 124. Controlling or regulating means or guide means is formed which regulating or guiding the outgoing direction of the fluid led to the forward end of the catheter body 122, to a direction of extension of the outgoing path 125.

As shown in FIG. 17, liquid or gas, indicated by arrows, gas-fed or liquid-fed from a location adjacent to a hand through the catheter body 122, can pass through the hollow portion 124 and the outgoing path 125 and can be blown toward the observe window 113 which is opposed to the outgoing path 125. Furthermore, water drops remaining on the observation window 13 can be sucked by the outgoing path 125 in the cap 123.

According to the seventh embodiment, the catheter body 122 passes through the channel 116, the cap 123 is brought to a condition projecting from the forward-end opening 118, and the outgoing path 125 is directed or oriented toward the observation window 113 to execute operation which operates the gas-feeding liquid-feeding suction unit (a foot switch is turned on, for example), whereby, as shown in FIG. 17, it is possible to blow fluid gas or liquid, toward the observation window 113 which is opposed to the outgoing path 125, as indicated by the arrows, and it is possible to remove extraneous matters or the like which are adhered to the outer surface of the observation window 113 and the like. That is, the seventh embodiment has cleaning function similar to that of an arrangement in which liquid or gas is jetted through a normal or usual nozzle.

In this manner, in case where, after having been used in observation of the affected or diseased parts or the like, the endoscope 101 is disinfected, the cleaning catheter 121 is taken out of the channel 116 in the endoscope 101, whereby, since the endoscope 101 has no bent nozzle portion, even if dirt flows into the channel 116, it is possible ensure that the endoscope 101 is disinfected. In case where the endoscope 101 is subsequently used, the cleaning catheter 121 after having been used is discarded, and a new cleaning catheter 121 should be used in place of the cleaning catheter after having been used. Specifically, in this embodiment, the cleaning catheter is brought to throwaway type.

Accordingly, the seventh embodiment has cleaning function similar to the arrangement in which liquid or gas is jetted through a normal or usual nozzle, and can easily and reliably execute the disinfection treatment of the endoscope. Further, according to the embodiment, since it is dispensed with to provide a nozzle on the endoscope in the conventional example, it is possible to reduce a diameter of particularly the forward-end portion of the endoscope, and it is possible to reduce or lighten pain given to patients at insertion and the like.

In connection with the above, as shown in FIG. 18, the arrangement may be such that a sign or mark 127 is provided on a portion of the catheter body 122 adjacent to a hand so as to be capable of setting the cap 123 to a position most adequate to clean the observation window 113, and a sign or mark (not shown) or the like is so provided as to facilitate setting of the orientation of the outgoing path 125 toward a direction of the observation window 113.

Figure 19:
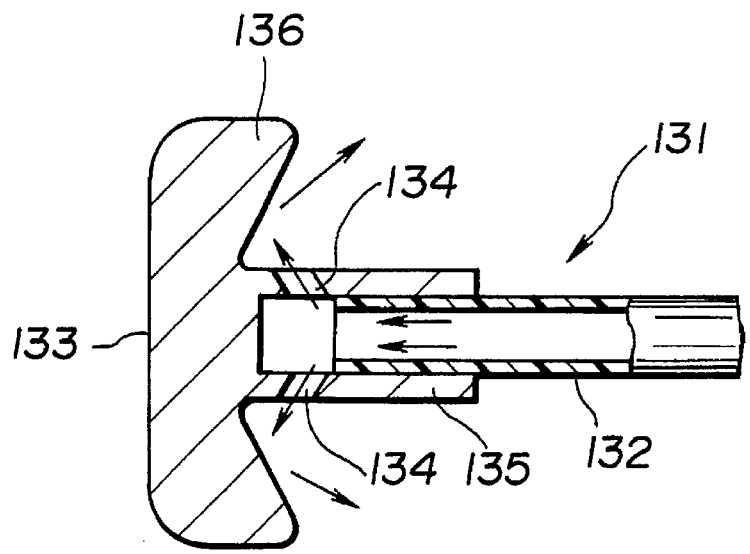
FIGS. 19 and 20 are views showing an eighth embodiment of the invention, FIG. 19 being a cross-sectional view showing an arrangement of a forward-end portion of a cleaning catheter according to the eighth embodiment.
Figure 20:
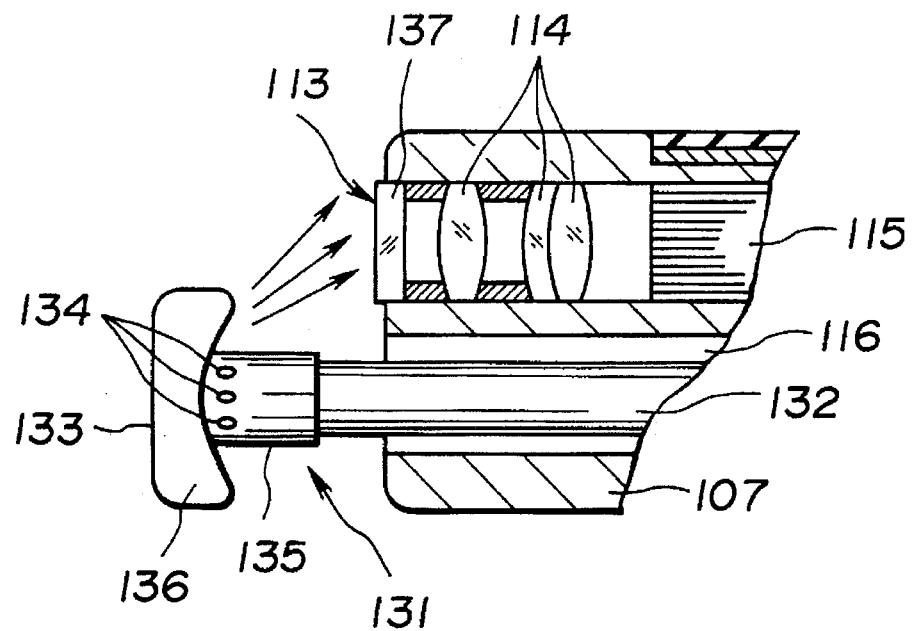

An eighth embodiment of the invention is shown in FIGS. 19 and 20.

A cleaning catheter 131 according to the eighth embodiment has a catheter body 132 formed by a flexible tube, and a cap 133 fixed to a forward end of the catheter body 132. The cap 133 is provided with a plurality of jetting openings 134, ... 134, as shown also in FIG. 20.

The cap 133 has a tube portion 135 in which the forward-end portion of the catheter body 132 is fitted and is firmly secured by adhesive or the like. The plurality of jetting openings 134, ... 134 communicating with the outside from the inside of the tube portion 135 are provided in a portion of the tube portion 135 just in front of the forward-end portion, so as to be oriented toward an outward direction obliquely forwardly. The cap 133 has a shade portion 136 which extends at an acute angle (an angle less than 90°) with respect to the tube portion 135, so as to be opposed against the various jetting openings 134 which are so provided as to be oriented outwardly obliquely forwardly, so that fluid passing through the jetting openings 134 are led to a direction around the forward-end portion of the catheter body 132 by an opposed surface (opposed to the jetting openings 134) in the shade portion 136.

In connection with the above, in case where the cleaning catheter 131 is so used as to be inserted into a channel 116 in the endoscope, a portion of the catheter body 132 adjacent to a hand is inserted from the forward-end opening in the channel 116, the portion adjacent to the hand projects from the inserting opening to the outside, and the projecting-end portion is connected to a mouthpiece of a gas-feeding liquid-feeding suction unit. Other arrangements are similar to those of the seventh embodiment. A forward-end portion 107 of the endoscope illustrated in FIG. 20 is similar in arrangement to that illustrated in FIG. 17, except that an observation window 113 is covered with a cover glass material 137.

In the embodiment, a portion of the cleaning catheter 131 adjacent to the forward end thereof projects from the forward-end opening of the channel 116 in the endoscope as illustrated in FIG. 20, whereby the fluid passing through the various jetting openings 134 change a jetting direction by the shade portion 136 so that the fluid can be abutted against the observation window 113. It is possible to clean or wash away and the like extraneous matters or the like on the outer surface of the cover glass material 137 which covers the observation window 113. In the embodiment, it is possible to also clean an illuminating window.

Advantages of the embodiment are substantially similar to those of the seventh embodiment. In this connection, the arrangement may be such that the plurality of jetting openings 134, ... 134 are provided on a portion in the peripheral direction.

Figure 21:
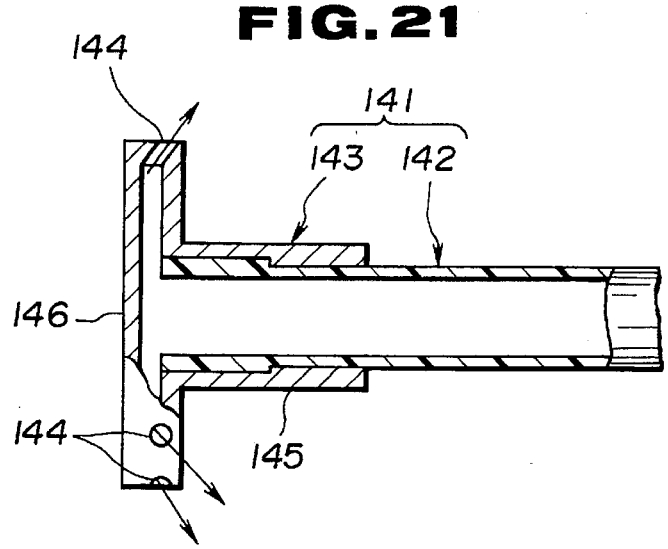
FIGS. 21 and 22 are views showing a ninth embodiment of the invention, FIG. 21 being a cross-sectional view showing an arrangement of a forward-end portion of a cleaning catheter according to the ninth embodiment.
Figure 22:
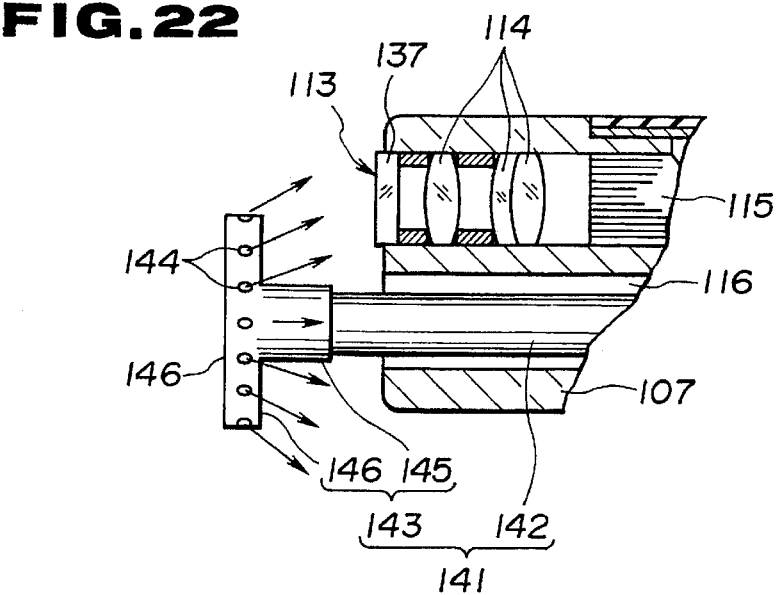

FIGS. 21 and 22 show a ninth embodiment of the invention.

A cleaning catheter 141 according to the ninth embodiment has a catheter body 142 formed by a flexible tube, and a cap 143 fixedly mounted on a forward end of the catheter body 142. As shown also in FIG. 22, the cap 143 is provided with a plurality of jetting openings 144, ... 144.

The cap 143 has a tube portion 145 in and on which the forward-end portion of the catheter body 142 is inserted and is fixedly mounted by adhesive or the like. An inner surface of the tube portion 145 adjacent to a top thereof is enlarged in diameter, and an enlarged step is provided on the outer peripheral surface of the forward-end portion of the catheter body 142 so that the cap 143 is prevented from coming off from the forward-end portion of the catheter body 142.

A hollow cap body 146 having a disc configuration is integrally formed on the top of the tube portion 145. The plurality of jetting openings 144, ... 144 communicating with the outside from the inside are provided in a side peripheral surface of the cap body 146, so as to be oriented toward the outside direction obliquely rearwardly. The arrangement is such that fluid passing through the various jetting openings 144 is led to a periphery of the forward-end portion of the catheter body 142 which is opposed to the jetting openings 144.

A portion of the cleaning catheter 141 adjacent to the forward end thereof projects from a forward-end opening of a channel 116 in the endoscope, as illustrated in FIG. 22, whereby the fluid passing through the various jetting openings 144 can be abutted against an observation window 113 which is opposed to the jetting openings 144. Thus, it is possible to clean a cover glass material 137 by washing-away or the like of extraneous matters and the like on the outer surface of the cover glass material 137 which covers the observation window 113. In this embodiment, the illuminating window can also be cleaned.

Advantages of the embodiment are similar to those of the eighth embodiment. In this connection, the arrangement may be such that the plurality of jetting openings 144, ... 144 are provided only a portion in the peripheral direction.

Figure 23:
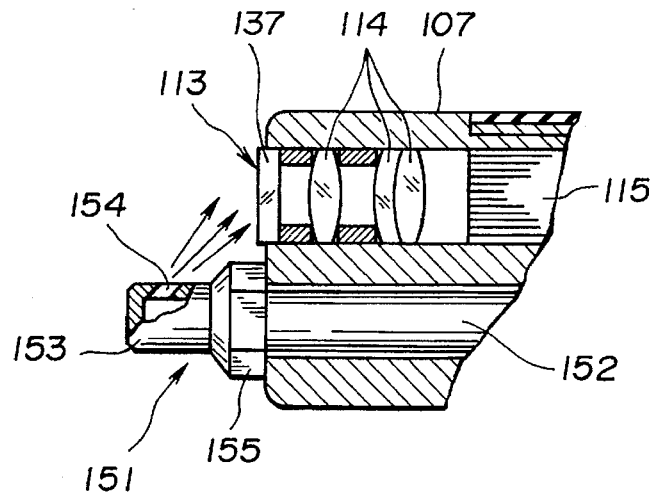
FIG. 23 is a view showing a tenth embodiment of the invention, a forward-end portion of an endoscope being shown under a condition that a cleaning catheter according to the tenth embodiment is mounted.

FIG. 23 shows a tenth embodiment of the invention.

A cleaning catheter 151 according to the tenth embodiment has a catheter body 152 formed by a flexible tube, and a cap 153 fixedly mounted on a forward end of the catheter body 152. The cap 153 is provided with a jetting port or opening 154.

The cap 153 has a tubular configuration in which a forward end of the cap 153 is closed. The cap 153 has a proximal end thereof in and on which the forward-end portion of the catheter body 152 is fitted and is fixedly mounted by adhesive or the like. The cap 153 has a side surface thereof adjacent to a top thereof, which is provided with the jetting opening 154 which communicates with the outside from the inside so as to be oriented in an outward direction obliquely rearwardly. The arrangement is such that fluid passing through the jetting opening 154 is led in a direction obliquely rearwardly which is opposed to the jetting opening 154.

The cap 153 has an outer peripheral surface thereof adjacent to the proximal end thereof, which is provided with a screw groove (not shown) on which a cap fixing tool 155 is mounted. The cap 153 can be fixedly mounted on the forward-end surface of the endoscope by the cap fixing tool 155. In the embodiment, the jetting opening 154 in the cap 153 is oriented toward a direction of an observation window 113, and the cap fixing tool 155 is screwed into the screw groove in the cap 153 to fix the orientation (rotational direction) of the cap 153, whereby, as shown in, for example, FIG. 23, orientation of the fluid jetted from the jetting opening 154 can be fixed in a direction toward the observation window 113, and a distance from the jetting opening 154 to the observation window 113 can be maintained constant. Thus, the endoscope can be maintained under a most adequate condition in which the observation window 113 is cleaned.

Other function and advantages are similar to those of the seventh embodiment.

FIGS. 24 to 30 show an eleventh embodiment of the invention.

Figure 25:
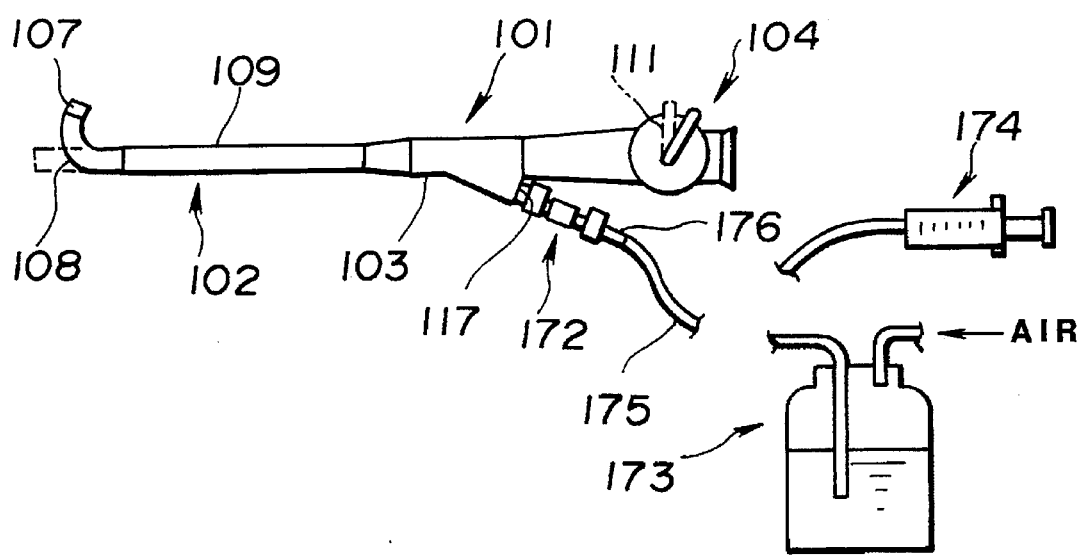

An endoscope 101 which is used in the embodiment illustrated in FIG. 25 is arranged similarly to the seventh embodiment. The same or identical reference numerals are applied to the same or identical components and parts, and the description thereof will be omitted.

Figure 24:
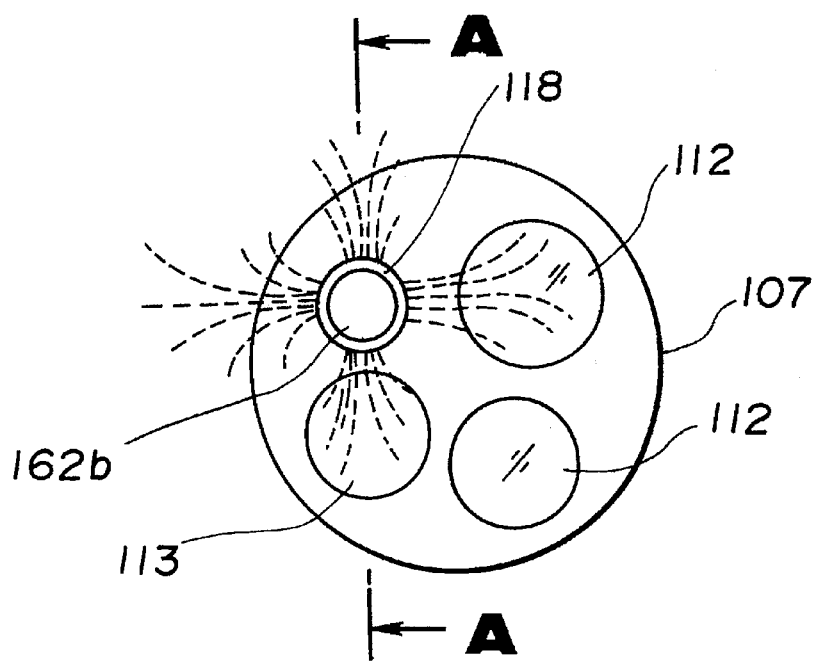
FIGS. 24 to 30 are views showing an eleventh embodiment of the invention, FIG. 24 being a view for explanation of operation at cleaning of a forward-end portion of an endoscope.
Figure 26:
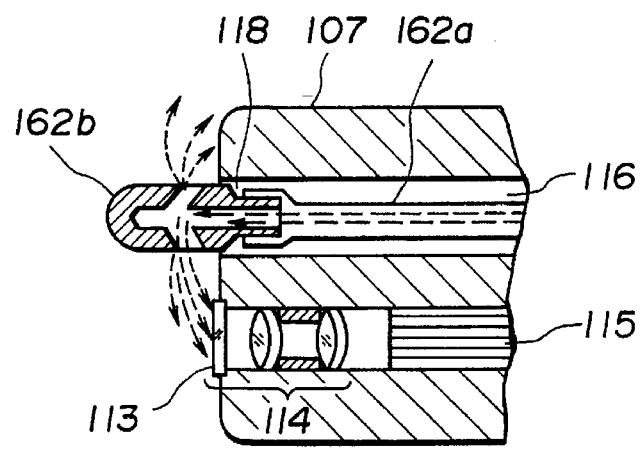
Figure 27:
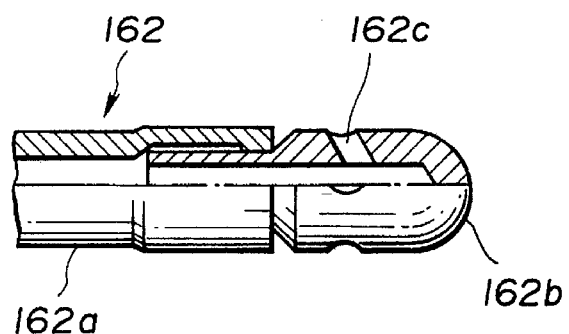

The endoscope 101 has a channel 116 which can be used as cleaning means. As shown in FIGS. 24 to 26, the cleaning means is inserted through a catheter body 162a of a cleaning catheter 162 to be described subsequently, from an inserting opening 117 in an operating section 103, to clean an outer surface of an observation window 113 or the like, that is, an outer surface of an objective lens system 114 and the like.

As shown in FIG. 25, the cleaning catheter 162 has a rearward end which is provided with water feeding means 173 capable of feeding cleaning water by a gas pressure. Further, gas-feeding suction means 174 such as a cylinder or the like is provided and is connected to a single gas-feeding and water-feeding tube 175. The gas-feeding and water-feeding tube 175 is connected to the cleaning catheter 162 through a mouthpiece 176. A positioning mechanism 172 for positioning an amount of insertion of the cleaning catheter 162 in a rearward and forward direction is provided at a part of the rearward end portion of the cleaning catheter 162, which is connected to the gas-feeding and water-feeding tube 175.

The cleaning catheter 162 has an elongated hollow catheter body 162a consisting of a tube insertable into the channel 116 and having flexibility, and a nozzle portion 162b which is provided adjacent to a forward end of the catheter body 162a, which is inserted into the channel 116 together with the catheter body 162a, and which is capable of being exposed from a forward-end portion 107 of an inserting section 102.

Furthermore, four jetting openings 162c are provided at equal intervals or in equally spaced relation to each other on the side surface of the nozzle section 162b peripherally. The four jetting openings 162c are capable of directing and jetting the cleaning fluid led from the catheter body 162a, toward the observation window 113 in the forward-end portion 107 and the like. In this connection, the cleaning jetting openings are not limited to four, but two, three or more than five cleaning jetting openings may be formed. Further, the cleaning jetting openings may be formed in the side surface of the nozzle portion peripherally so as to be spaced from each other axially.

Figure 28:
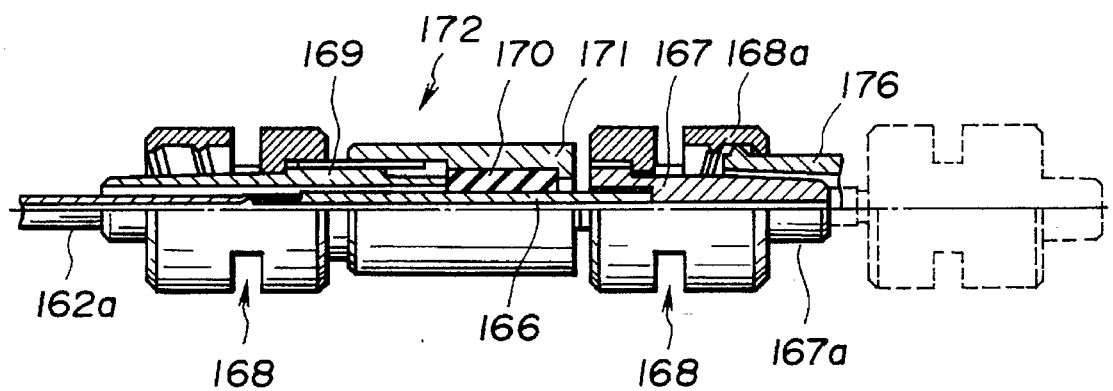

As shown in FIG. 28, a hollow pipe 166 thick or large in diameter is connected to a rearward-end portion of the catheter body 162a. The hollow pipe 166 has a rearward-end portion thereof to which a hollow joining pipe 167 having an outer periphery formed with a joining tapered surface 167a is connected. Furthermore, the joining pipe 167 is provided with a joining nut 168a at a location adjacent to the joining tapered surface 167a. A fixable nut assembly 168 is arranged at the joining pipe 167.

Moreover, the catheter body 162a has a rearward end thereof at which the hollow pipe 166 is provided whose outer periphery is provided with an urging pipe 169 having an inner diameter through which the hollow pipe 166 is slidable and having an outer periphery formed with a threaded portion, and a hollow-pipe fixing element 170 urged against the urging pipe 169 and formed by a deformable elastic material such as silicon rubber or the like. A thumb portion 171 is provided which houses therein the hollow-tube fixing element 170 and which is provided with a screw or threaded portion threadedly engageable with a threaded portion of the urging pipe 169. Furthermore, the thumb portion 171 has an end surface thereof which is abutted against the threaded portion of the urging pipe 169, and the nut assembly 168 similar to that used to fix the joining pipe 167 is fixed to the threaded portion of the urging pipe 169 in order to control or restrain an amount of sliding movement of the thumb portion 171.

Specifically, the nut assembly 168, the urging pipe 169, the hollow-pipe fixing element 170 and the thumb portion 171 cooperate with each other to form a positioning mechanism 172 for positioning an amount of insertion of the cleaning catheter 162 within the channel 116 thereof in a forward and rearward direction.

Operation of the arrangement described above will next be described.

First, when observation due to the endoscope 101 is executed, the nozzle portion 162b and the catheter body 162a of the cleaning catheter 162 are inserted into the channel 116 in the endoscope 101. Specifically, the cleaning catheter 162 is inserted into the opening 118 in the forward-end section 107 of the endoscope adjacent to an end thereof from the inserting opening 117 of the channel 116 through the inserting section 102. The nozzle portion 162b of the cleaning catheter 162 projects from the opening 118. The jetting openings 162c in the nozzle portion 162b are directed toward the observation window 113 in the forward-end portion 107, and the like.

Figure 29:
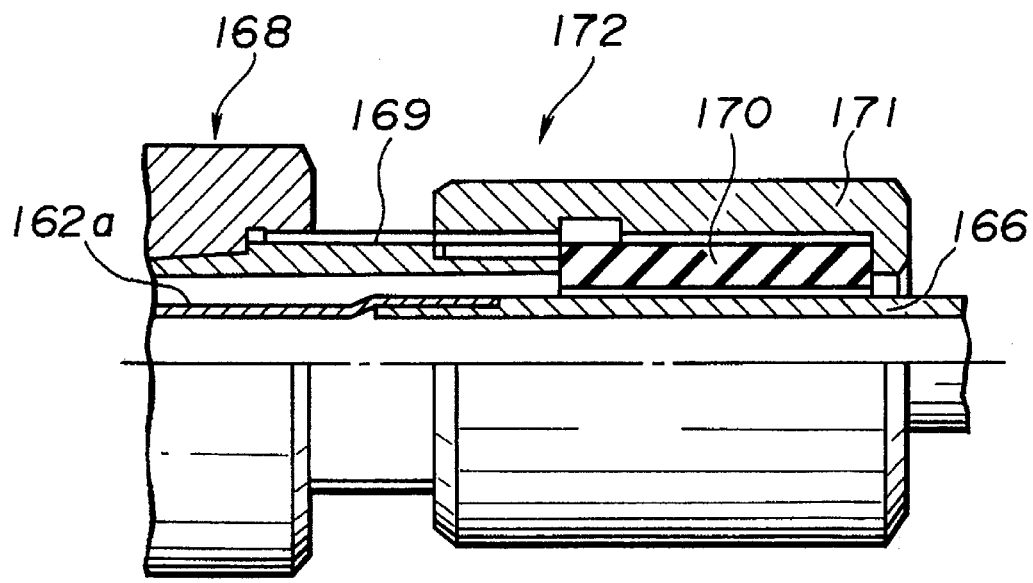
Figure 30:
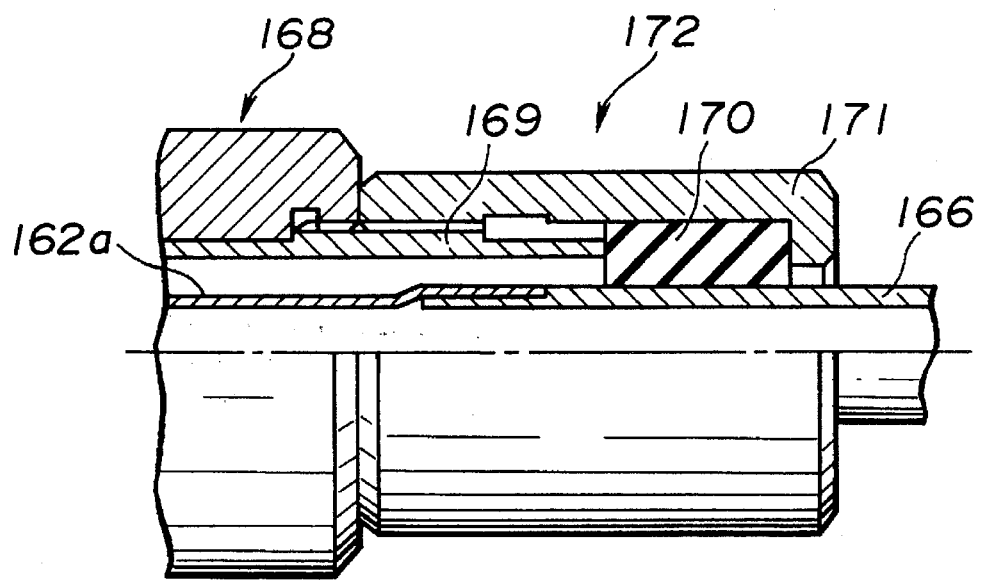

If a projecting position is determined or decided, the thumb portion 171 of the positioning mechanism 172 is rotatively moved along the threaded portion of the urging pipe 169 of the thumb portion 171. Then, by the movement of the thumb portion 171, the end surface of the urging pipe 169 urges the hollow-pipe fixing element 170 to deform the latter. By this deformation, the hollow pipe 166 at the rearward end of the catheter body 162a is fixed. Further, the thumb portion 171 of the positioning mechanism 172 is moved until the end surface of the thumb portion 171 is abutted against the nut assembly 168 adjacent to the operating portion 108. As a result, it is ensured that the projecting position of the nozzle portion 162b is decided and fixed. In this connection, FIG. 29 shows a condition under which the positioning mechanism 172 is loosened, while FIG. 30 shows a condition at time the positioning mechanism 172 is tightened and fixed.

Subsequently, in case where filth or dirt, or the like is deposited or adhered to the observation window 113 in the endoscope 101, and the like, during observation due to the endoscope 101, the cleaning water is fed into the gas-feeding and water-feeding tube 175 by a gas pressure, due to the water feeding means 173, to feed the water into the cleaning catheter 162. The cleaning water is jetted from the jetting opening 162c which is formed in the nozzle portion 162b of the cleaning catheter 162, to remove dirt or the like on the observation window 113.

Furthermore, also in case where gas is supplied for the purposes of removal of the water drops after cleaning, and the like, the gas is similarly supplied or fed into the gas-feeding and water-feeding tube 175 by the gas-feeding suction means 174 such as a cylinder or the like. The gas is fed into the cleaning catheter 162 so that the gas is jetted from the jetting openings 162c formed in the nozzle portion 162b of the cleaning catheter 162, to remove the water drops and the like on the observation window 113. Moreover, suction is made by the jetting opening 162c similar to the first embodiment, whereby it is also possible to remove the water drops remaining on the observation window 113.

Here, since the four (4) jetting openings 162c are formed peripherally on the nozzle portion 162b, it is possible to ensure that the cleaning fluid is jetted toward the observation window 113, even if the cleaning catheter 162 shifts peripherally within the channel 116 in the endoscope 101, by curvature of the endoscope curving portion 108 and the like. Further, the arrangement may be such that, by provision of many cleaning jetting openings, jetting of the fluid toward the observation window is further ensured.

Furthermore, since existing channel in an endoscope and a forward-end portion thereof can be used as they are as the above-described channel and forward-end portion, without the necessity of particularly guide means and the like, the cleaning catheter apparatus can be brought to one in which general-purpose uses and interchangeability are superior.

Moreover, since the cleaning catheter is easily detached or demounted from the endoscope and can be treated in cleaning and disinfection, there can be produced a further clean and sanitary cleaning function.

FIGS. 31 through 34(a) and 34(b) shows a twelfth embodiment of the invention.

Figure 31:
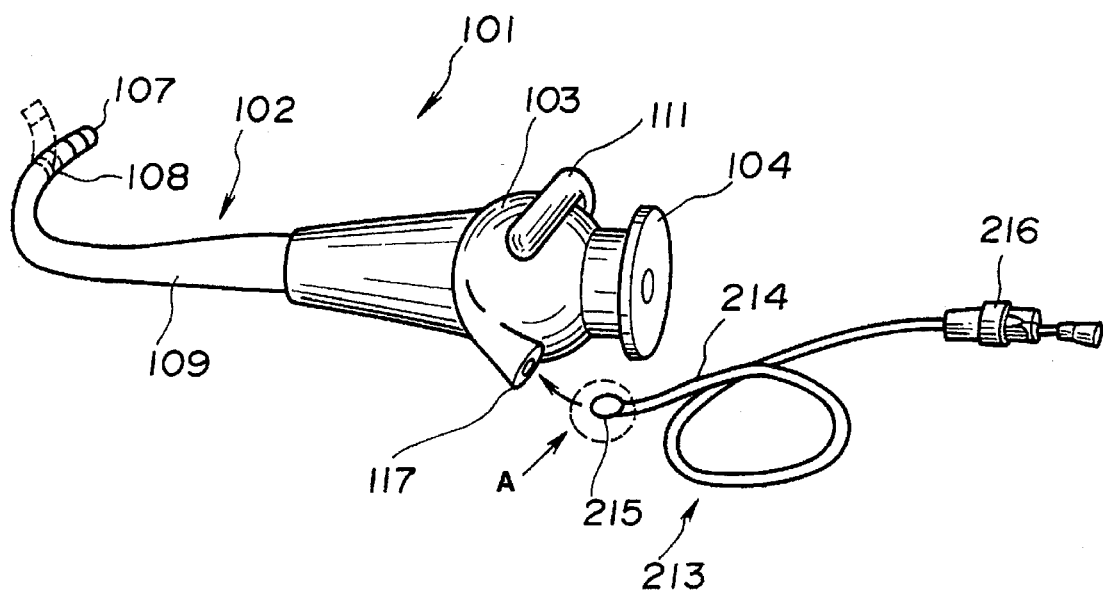
FIGS. 31 to 34 are views showing a twelfth embodiment of the invention, FIG. 31 being a view for explanation, showing an arrangement of an entire endoscope apparatus.

An endoscope 101 which is used in the present embodiment illustrated in FIG. 31 is arranged similarly to the seventh embodiment. The same or identical reference numerals are applied to the same or identical components and parts, and the description thereof will be omitted.

A cleaning tube 213 to be described subsequently is inserted into a channel provided in the endoscope 101 from an inserting opening 117 in an operating portion 103 so that the cleaning tube 213 can be used as cleaning means for cleaning an outer surface or the like of an observation window in a forward-end portion of an inserting section 107, that is, an outer surface and the like of an observation optical system.

The cleaning tube 213 is so arranged as to comprise a tube body 214 insertable into the channel and serving as an elongated hollow tube portion having flexibility, a forward-end tip 215 provided adjacent to the forward end of the tube body 214, inserted into the channel together with the tube body 214, and serving as a fluid jetting portion capable of being exposed from the forward-end portion 107 of the inserting section 102, and a fixing portion 216 provided adjacent to the rearward end of the tube body 214, for fixing an end of the cleaning tube 213 at a hand, to the inserting opening 117 in the endoscope 101. The cleaning tube 213 is connected to fluid supply means (not shown) for supplying cleaning fluid such as cleaning liquid, air or the like. The arrangement is such that the cleaning liquid and the like form the fluid supply means is jetted from the forward-end tip 215 through the tube body 214.

Figure 32:
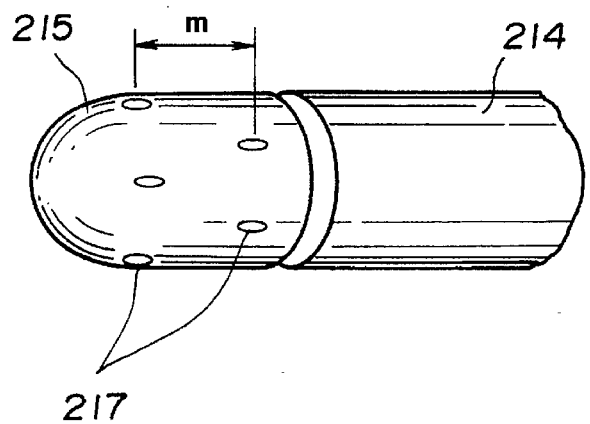

FIG. 32 is a view in enlargement showing a portion A in FIG. 31. The forward-end tip 215 is formed with a plurality of jetting openings 217 for jetting the cleaning liquid or the like, in a peripheral configuration axially in two rows. A distance m between the two rows of the jetting openings 217 is so set as to correspond to a variation width of an amount of projection of the forward-end tip 215 from the forward-end portion 107 of the endoscope, which occurs in case where a curving portion 108 of the inserting section 102 is operated in curvature, when the cleaning tube 213 is inserted into the channel in the endoscope 101 so that the forward-end tip 215 projects from the forward-end portion. Further, the jetting openings 217 arranged in two rows as described previously are alternately provided so as not to be overlapped with each other in a peripheral direction.

In connection with the above, the plurality of jetting openings are not so limited as to be arranged in two rows axially, but may be arranged in a plurality of rows within a range or extent of the variation width of the amount of projection of the cleaning tube due to the curvature operation of the curving portion.

Figure 33A:
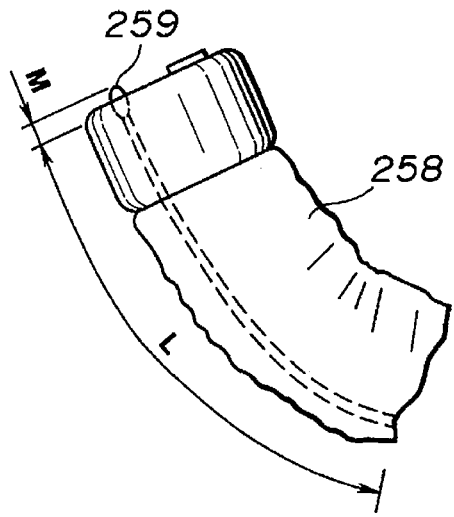
Figure 33B:
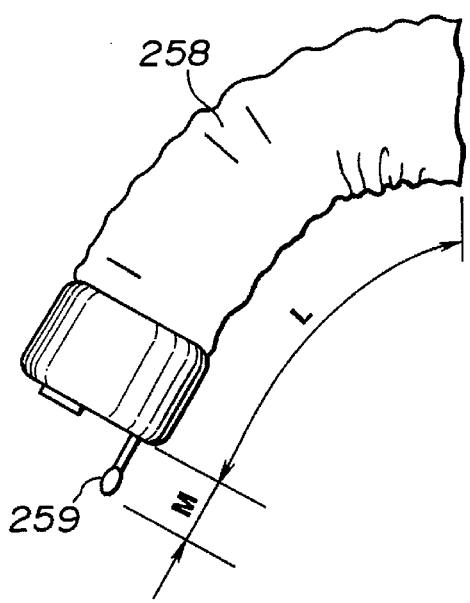

As shown in FIG. 33(a) and 33(b), only mere insertion of the cleaning tube into the channel in the endoscope varies an amount of projection M of the forward-end portion 259 of the cleaning tube from the forward end of the inserting section, because, when the forward-end portion 258 of the inserting section is operated in curvature, a length L of the channel into which the cleaning tube is inserted varies. For this reason, there is a case where the jetting openings provided in the forward-end portion 259 of the cleaning tube an retracted into the channel in the endoscope, and there occurs a problem that the objective lens cannot be cleaned. Accordingly, it is necessary to set the amount of projection of the forward-end portion 259 of the cleaning tube, in accordance with the amount of curvature of the inserting section. Such setting of the amount of projection is cumbersome and troublesome, and operability is not good or excellent. In view of this, the embodiment intends to solve the above-described problem, by the fact that a plurality of jetting openings are formed axially.

Figure 34A:
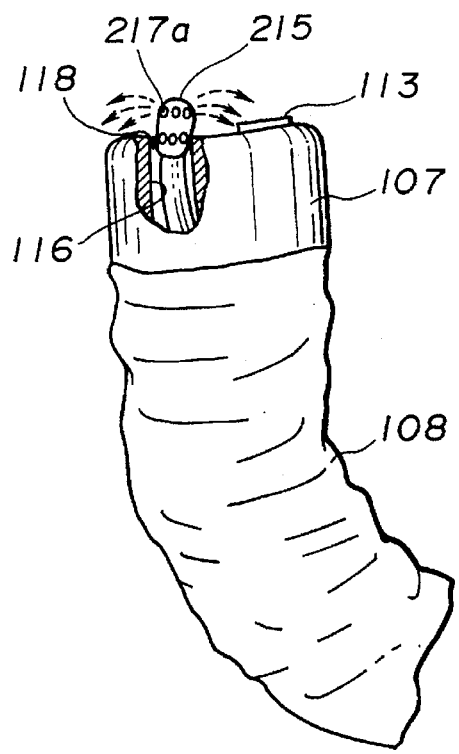
Figure 34B:
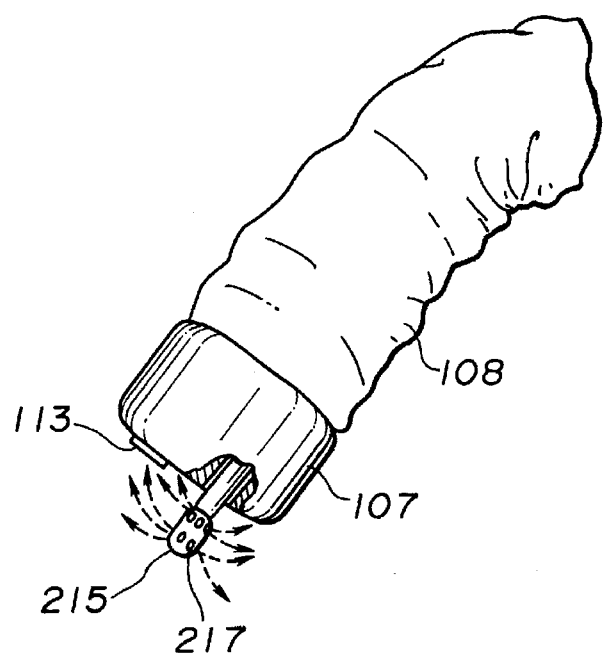

In case where the observation optical system of the endoscope 101 is cleaned by the cleaning tube 213, the cleaning tube 213 is first inserted from the inserting opening 117 in the endoscope 101, the forward-end tip 215 of the tube projects from the forward end of the inserting section 102, and an end of the cleaning tube 213 at a hand is fixed to the inserting opening 117 by the fixing portion 216. Cleaning fluid is supplied to the cleaning tube 213 by fluid supply means (not shown). The cleaning fluid is outgone from the injection openings 217 in the forward-end tip 215 which projects from the opening 118 at the forward end of the forward-end portion 107 of the endoscope, as shown in FIGS. 34(a) and 34(b). The outgoing fluid reaches the observation window 113 in the forward end of the inserting section, and the like, to clean the forward end of the inserting section including the observation optical system.

Here, when the curving portion 108 is curved downwardly, that is, toward the channel through which the cleaning tube 213 is inserted, as shown in FIG. 34(b), the forward-end tip 215 sufficiently projects from the forward end of the inserting section, so that it is possible to jet the cleaning fluid from the jetting openings 217 to sufficiently clean the forward end of the inserting section, such as the observation window 113 or the like.

Further, when the curving portion 108 is curved upwardly, that is, opposite to the channel through which the cleaning tube 213 is inserted, as shown in FIG. 34(a), a portion of the forward-end tip 215 adjacent to the proximal end thereof enters the channel 116. However, the portion of the forward-end tip 215 adjacent to the forward end thereof projects from the forward end of the inserting section. When the cleaning fluid is fed, the cleaning fluid is jetted from the jetting openings 217a adjacent to the forward end of the inserting section. Thus, the forward end of the inserting section including the observation window 13 is cleaned.

In this manner, in the cleaning tube which leads the cleaning fluid to the forward-end portion of the endoscope to execute cleaning, the plurality of jetting openings are formed axially which jet the cleaning fluid to the observation optical system at the forward-end portion of the endoscope, and the like, whereby it is not necessary to adjust or regulate an amount of projection of the forward-end tip at a hand each time the curving operation is executed. Only first fixing of the amount of projection enables the cleaning fluid to be jetted to the observation optical system from at least one jetting opening even under all of curving conditions. Thus, even in case where the amount of curvature of the inserting section of the endoscope changes, it is possible to ensure that the observation optical system is cleaned. Further, the jetting openings are formed also peripherally and, accordingly, even in case where torsion occurs in the inserting section of the endoscope, it is possible to jet the cleaning fluid to the observation optical system. The cleaning tube is insertable into the channel in the endoscope. It is possible to use the cleaning tube for new one such as throwaway ones every cases of a disease, and it is possible to use the cleaning tube after having been disinfected and sterilized. Thus, a clean condition can be maintained. Furthermore, since it is unnecessary to set the amount of projection of the forward-end tip and the direction of the jetting openings each time the amount of curvature changes, handling is simple, operability is superior, and the apparatus can also be arranged simply.

FIGS. 35(a), 35(b) and 35(c) to 37 show a thirteenth embodiment of the invention.

The thirteenth embodiment is an example in which an arrangement of a forward-end tip of a cleaning tube and an arrangement of a fixing portion at a rearward end of the cleaning tube are modified.

As shown in FIG. 35, a cleaning tube 221 is arranged such that a cylindrical forward-end tip 222 having a forward end thereof which is spherical and which is closed is connected to the inside of a tube body 223 by threaded engagement. The forward end 222 is formed therein with jetting ports or openings 224 peripherally at intervals of 90° in two rows axially. As shown in FIG. 35(a)–35(c), the jetting openings 224 in two rows are provided in a configuration shifting through 45° peripherally. Moreover, the jetting openings 224 are so formed as to be inclined rearwardly, and so open as to be directed obliquely rearwardly. Thus, the cleaning fluid introduced through the cleaning tube 221 is jetted obliquely rearwardly.

Figure 36:
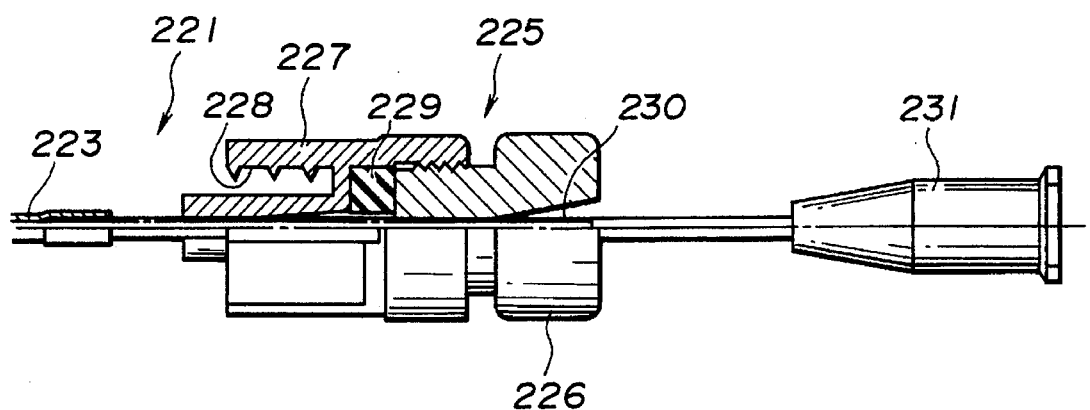

As shown in FIG. 36, a fixing portion 225 is provided adjacent to the rearward end of the cleaning tube 221. The fixing portion 225 has a fixing thumb 226 held at being fixed to an inserting opening 117 in the endoscope, a connecting element 227 connected to the fixing thumb 226 in threaded engagement and having a threaded portion 228 threadedly engageable with the inserting opening 117 at a location on the inside of the forward-end portion, and a tightening element 229 having elasticity and provided between the forward end surface of the fixing thumb 226 and a step on the connecting element 227 on the inside thereof. A pipe section 230 connected to a proximal end of the tube body 223 is slidably inserted in a pipe cavity portion in the fixing portion 225. The arrangement is such that rotation of the fixing thumb 226 deforms the tightening element 229 in a direction along a central axis, so that the pipe portion 230 can be tightened and fixed. Further, a cylinder connecting portion 231 for connecting a cylinder serving as fluid supply means is connected to a location adjacent to the rearward end of the pipe portion 230.

Figure 37:
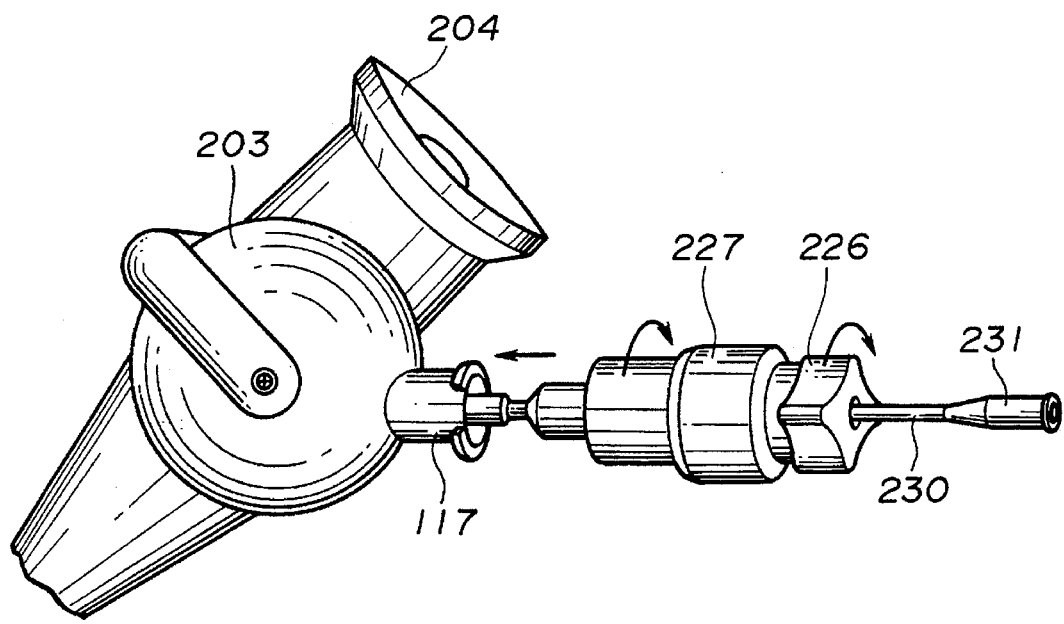

In case where the observation optical system of the endoscope 101 is cleaned by the cleaning tube 221, as shown in FIG. 37, the tube body 223 including the forward-end tip 222 is first inserted from the inserting opening 117 in the endoscope 101, and the connecting element 227 of the fixing portion 225 is rotated in a direction indicated by an arrow in FIG. 37 to threadedly engage the threaded portion 228 with the inserting opening 117 to mount the threaded portion 228, whereby the fixing portion 225 is fixed to the inserting opening 117. The tube body 223 of the cleaning tube 221 and the pipe portion 230 are slidingly moved forwardly and rearwardly, to decide an amount of projection of the forward-end tip 222 from the forward end of the inserting portion. Under this condition, the fixing thumb 226 is rotated in a direction arrowed in FIG. 37, whereby the tightening element 229 is deformed toward the central axis, and the pipe portion 230 is tightened and is fixed within the fixing portion 225. Thus, the tube body 223 and the pipe portion 230 are fixed in position axially with respect to the fixing portion 225 and the inserting opening 117.

Subsequently, a cylinder (not shown) is connected to the cylinder connecting portion 231, and the cleaning fluid is fed into the cleaning tube 221 by the cylinder. Then, the cleaning fluid is led through the tube body 223, reaches the forward-end tip 222, and is jetted obliquely rearwardly from the jetting opening 224. By doing so, the clearing fluid impinges energetically against the forward end of the inserting section so that filth or dirt on the forward end of the inserting section including the observation window is removed.

In this manner, the plurality of jetting openings are formed axially similarly to the twelfth embodiment, whereby, even under all of curved conditions, it is possible to jet the cleaning fluid to the observation optical system from at least one jetting opening. Thus, even in case where the amount of curvature of the inserting section of the endoscope changes, it is possible to ensure that the observation optical system is cleaned. Further, since the jetting openings are so formed as to be directed obliquely rearwardly, it is possible to cause the cleaning fluid to impinge energetically against the observation window. Thus, it is also possible to sufficiently remove dirt which is difficult to be removed. Furthermore, by the fixing portion, it is possible to fix the positions of the cleaning tube and the channel opening, it is possible to position the amount of projection of the forward end tip, and it is possible to prevent the cleaning tube from coming off from the channel during the use.

Other arrangements, function and advantages are similar to those of the twelfth embodiment.

Figure 38:
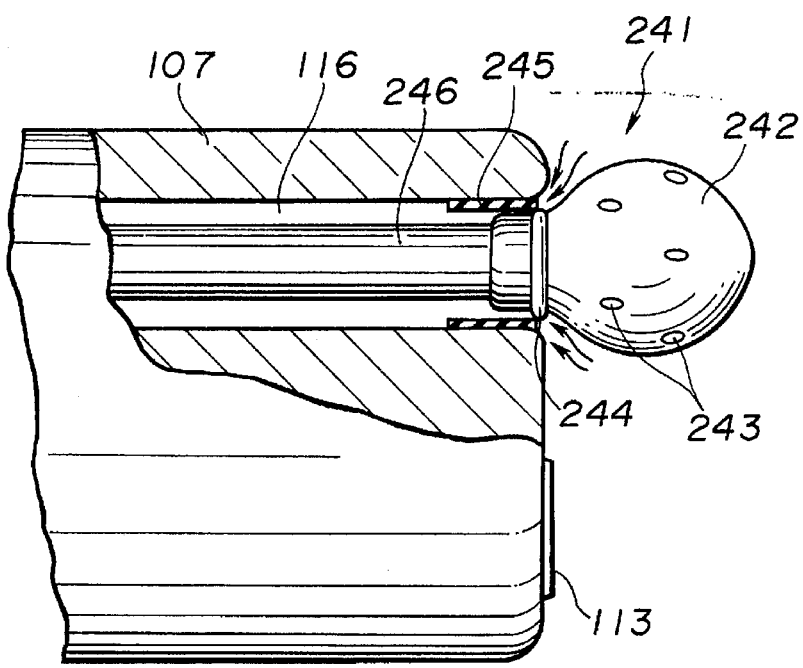
FIG. 38 is a view showing a fourteenth embodiment of the invention, and is a partially cut-away cross-sectional view showing an arrangement of a forward-end portion under a condition in which a cleaning tube is inserted into a channel in an endoscope.

FIG. 38 shows a fourteenth embodiment of the invention, and is a partially broken-away cross-sectional view showing an arrangement of a forward-end portion under a condition that a cleaning tube is inserted into a channel in an endoscope.

Similarly to the twelfth embodiment, a cleaning tube 241 according to the fourteenth embodiment is arranged such that a plurality of jetting openings 243 are formed in two rows axially in a forward-end tip 242, while an O-ring portion 244 is provided at a proximal-end portion of the forward-end tip 242. Further, a ring fitting portion 245 which is formed by rubber or the like in which the O-ring portion 244 is resiliently fitted is provided in an opening at the forward end of the channel 116 in the endoscope. Specifically, at least one of the O-ring portion 244 and the ring fitting portion 245 has elasticity, and the O-ring portion 244 and the ring fitting portion 245 are tightly fitted in each other so that air-tightness is maintained. In this connection, the cleaning tube 241 is arranged such that a tube body 246 is inserted into a channel 116 to project from the forward end of the inserting section and, subsequently, the forward-end tip 242 is mounted on the tube body 246.

In this embodiment, at cleaning, the tube body 246 is first inserted into the channel 116 in the endoscope and projects from the forward end of the inserting section, and the forward-end tip 242 is mounted on the tube body 246. Subsequently, the cleaning tube 241 is drawn into the side of a hand, the O-ring portion 244 is tightly fitted in the ring fitting portion 245, and the forward-end opening of the channel 116 is air-tightened. The cleaning fluid is supplied to the cleaning tube 241 by the fluid supply means, and is jetted from the jetting openings 243 in the forward-end tip 242, to clean the forward end of the inserting section including the observation optical system. At this time, since the forward end opening of the channel 116 is maintained air-tight, there is no case where blood, dirt and the like do not entire the channel 116.

In this manner, the plurality of jetting openings are formed axially, whereby it is possible to jet the cleaning fluid to the observation optical system from at least one jetting opening even under all of the curved conditions. Thus, the fourteenth embodiment has advantages similar to those of the twelfth embodiment. Furthermore, since it is possible to maintain the forward-end opening of the channel air-tight by the O-ring portion and the ring fitting portion, it is possible to prevent filth, dirt and the like from entering the channel, making it possible to maintain the endoscope clean.

Other arrangements and function are similar to those of the twelfth embodiment.

Figure 39:
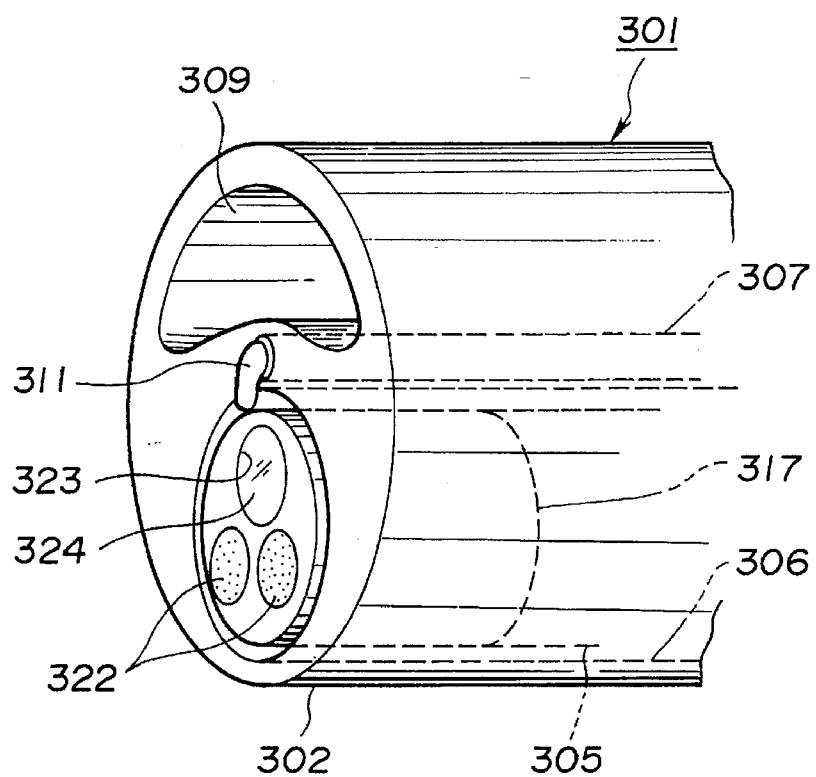
FIGS. 39 and 40 are views showing a fifteenth embodiment of the invention, FIG. 39 being a view for explanation, showing a forward-end portion of a cleaning tube under a condition in which an endoscope is mounted on a cleaning catheter according to the fifteenth embodiment.
Figure 40:
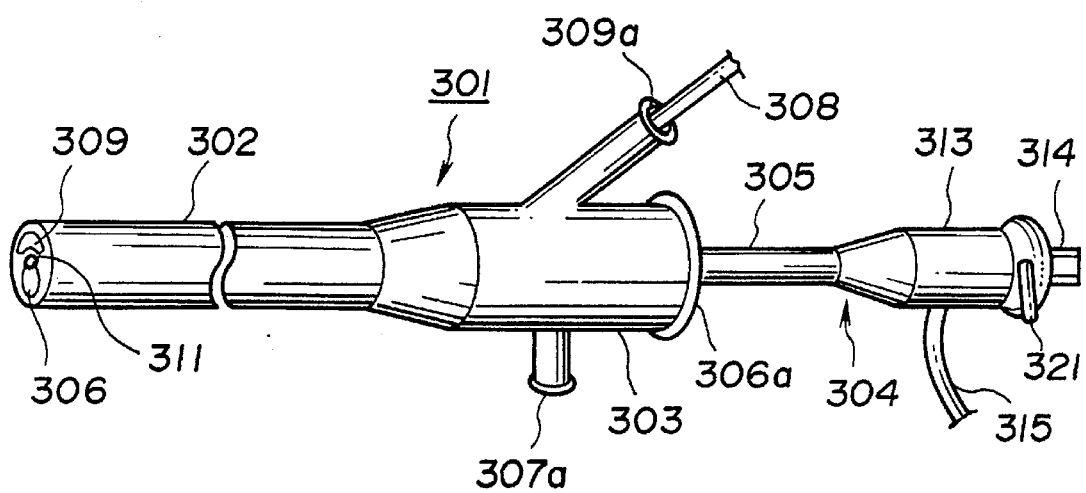

FIGS. 39 and 40 show a fifteenth embodiment of the invention.

In the fifteenth embodiment, an endoscope is so arranged as to have a catheter serving as a guide tube provided with a plurality of lumens, and an endoscope body (hereinafter, this will be referred to as merely an "endoscope") which is inserted in one of the lumens in the catheter.

As shown in FIG. 40, the catheter 301 according to the fifteenth embodiment has an elongated catheter section 302, and a holding section 303 large in diameter and connected to a rearward end of the catheter section 302. The catheter section 302 has a first lumen 306 in which an inserting section 305 of the endoscope 304 is insertable, a second lumen 307 for leading fluid, and a third lumen 309 in which a treatment tool 308 and the like are insertable.

The second lumen 307 has a forward-end opening thereof on which a nozzle 311 is mounted. The arrangement is such that the fluid led to a portion of the second lumen 307 therethrough adjacent to a forward end thereof can be outgone toward a forward-end opening of the first lumen 306 through the nozzle 311, which is located opposite to the outgoing end of the nozzle 311.

The holding section 303 of the catheter 301 is provided with an opening end 306a communicating with the first lumen 306, an opening end 307a communicating with the second lumen 307, and an opening end 309a communicating with the third lumen 309. The inserting section 305 of the endoscope 304 can be inserted in the opening end 306a, a tube connected to a cleaning unit (not shown) is insertable in the opening end 307a, and the treatment tool 308 is insertable in the opening end 309a.

On the other hand, as shown in FIG. 40, the endoscope 304 for, for example, observing a pleural cavity, which is so used as to be inserted into the first lumen, has the elongated inserting section 305 having built therein observing means and having flexibility, an operating section 313 large in width and connected to a rearward end of the inserting section 305, an ocular or eyepiece section 314 formed at a rearward end of the operating section 313, and a light guide cable 315 extending from a side of the operating section 313. A connector (not shown) which is mounted on an end of the light guide cable 315 is detachably connected to a light source unit.

The inserting section 305 has, from a forward end thereof, a hard forward-end portion 317 (refer to FIG. 39), a curving portion capable of being curved, and a flexible flexing pipe portion. A curving knob 321 provided on the operating section 313 is operated, whereby the curving portion can be curved.

The arrangement is as follows. That is, the light guide cable 315 has the connector which is connected to the light source unit, whereby white light from a lamp (not shown) within the light source unit is illuminated to an end surface of the light guide. The illuminating light transmitted by the light guide is outgone forwardly from a pair of illuminating windows 322 and 322 on which the end surface adjacent to the forward-end portion 317 is mounted, to illuminate a subject part (not shown).

An optical image of the subject part which is illuminated by the illuminating light is focused on one of a pair of end surfaces of the image guide which is fixed to a focusing surface of an objective lens 324 illustrated in FIG. 39, which is mounted on the observation window 323 in the forward-end portion 317, by the objective lens system 324. The optical image is transmitted to the other end surface adjacent to the ocular portion 314, by the image guide. An ocular or eyepiece lens (not shown) is arranged in opposed relation to the other end surface. Thus, it is possible to observe, in enlargement, the subject part through the ocular lens by the naked eye.

The fifteenth embodiment is characterized in that the inserting section 305 of the endoscope 304 is inserted into the first lumen 306 of the catheter 301, so as to be used as cleaning means for cleaning the outer surface of the observation window 323, that is, the outer surface of the objective lens system 324. Specifically, as shown in FIG. 40, if the inserting section 305 of the endoscope 304 is inserted into the first lumen 306 so that the forward-end surface thereof is set to a location confronted with the opening end of the first lumen 306, it is possible to oppose a bent outgoing opening of the nozzle 311 mounted on the opening at the forward end of the second lumen 307, against the observation window 323 at the forward end surface thereof. Thus, the fluid is supplied from a portion of the second lumen 307 at a hand, whereby it is possible to blow the fluid against the observation window 323 which is opposed to the outgoing opening.

According to the fifteenth embodiment, the inserting section 305 of the endoscope 304 is inserted into the first lumen 306 of the catheter 301, whereby, as shown in FIG. 39, it is possible to set the observation window 323 so as to be opposed to the outgoing opening of the nozzle 311. Under this condition, liquid or gas is fed out toward a portion adjacent to the forward end through the second lumen 307, whereby it is possible to blow the liquid or gas against the observation window 323. Thus, it is possible to clean or remove extraneous matters which are adhered to the outer surface of the observation window 323, or the like. Further, the liquid or gas is sucked from the outgoing opening of the nozzle 311, whereby it is possible to remove remaining water drops.

That is, the fifteenth embodiment has cleaning function similar to that of the conventional arrangement in which liquid or gas is jetted through a nozzle provided in a forward end of an endoscope.

In this manner, in case where the endoscope 304 is used in observation of the affected or diseased parts and, subsequently, the endoscope 304 is disinfected, the endoscope 304 takes or pulls out from the catheter 301, whereby it is possible to ensure that the endoscope 304 is disinfected because the endoscope 304 has no curved nozzle portion. Furthermore, in this embodiment, since a detachable mechanism is not provided adjacent to the forward end of the endoscope 304, there is almost no danger that the detachable mechanism (cap or the like in the conventional example) comes off or falls off during the use.

In connection with the above, in case where the endoscope 304 is next used, the used catheter 301 is discarded, and a new catheter 301 should be used. That is, in this embodiment, the catheter 301 is a throwaway one.

Accordingly, the fifteenth embodiment has cleaning function similar to an arrangement in which liquid or gas is jetted through a nozzle provided in a forward end of a conventional endoscope. It is possible for this embodiment to completely treat, in disinfection, the endoscope 304 by simple operation.

Figure 41:
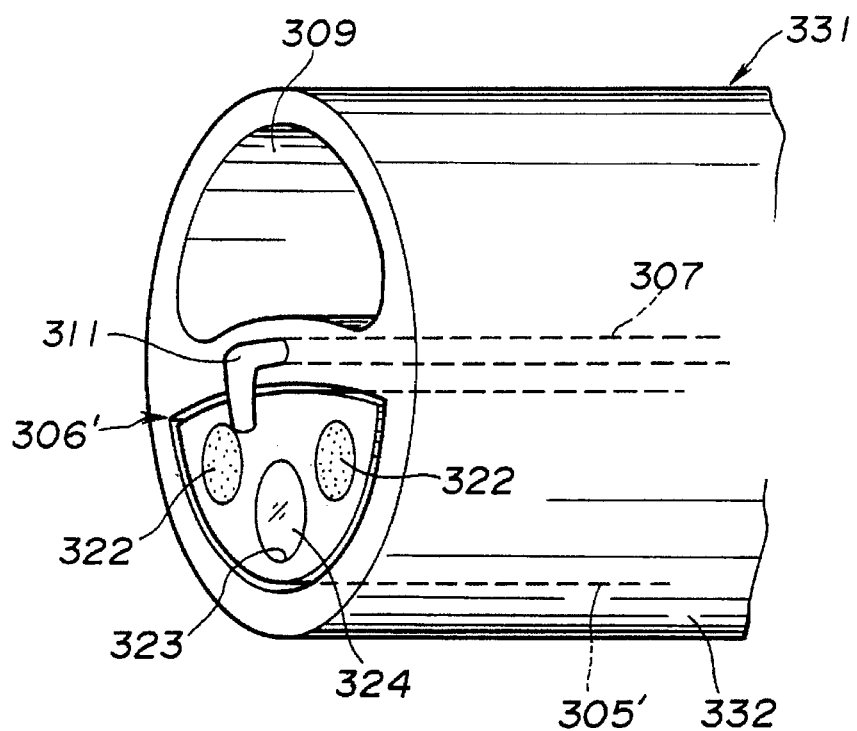
FIG. 41 is a view showing a modification of the fifteenth embodiment of the invention, and is a view for explanation, showing a forward-end portion of a cleaning tube under a condition in which an endoscope is mounted on a cleaning catheter.

FIG. 41 shows a modification of the fifteenth embodiment of the invention.

A catheter 331 of this modification comprises a catheter portion 332 formed by a flexible tube, and a holding portion (not shown) connected to a rearward end of the catheter portion 332. Similarly to the fifteenth embodiment, this modification has a first lumen 306' in which an inserting section 305' (of an endoscope) is insertable, a second lumen 307 for leading fluid, and a third lumen 309 in which a treatment tool or the like is insertable.

A nozzle 311 is mounted on an opening end of a forward end of the second lumen 307. Fluid led to a portion of the second lumen 307 adjacent to the forward end thereof through the second lumen 307 passes through the nozzle 311, and can be outgone toward a portion of the first lumen 306' adjacent to the opening in the forward end thereof, which is opposed to a portion of the nozzle 311 adjacent to an outgoing end thereof.

The modification is characterized as follows. That is, the first lumen 306' of the catheter 331 is arranged such that an inner cavity of the lumen is a heteromorphic configuration different from center symmetricalness, as shown, and the heteromorphic configuration is similar to an outer configuration of the inserting section 305' (of the endoscope). The inserting section 305' passes through the first lumen 306' so that the forward-end surface of the inserting section 305' is set to a location facing toward the opening end of the first lumen 306' at the forward end thereof, whereby it is possible to (automatically) set the outer surface of the observation window 323 at the forward-end surface of the first lumen 306' (that is, an outer surface of the objective lens system 324), to a location which faces toward the outgoing opening of the nozzle 311. By fluid jetted through the outgoing opening, it is possible to clean the observation window 323. In this connection, the arrangement may be such that the portions having the heteromorphic configuration include only the forward-end portion of the inserting section 305', and a portion of the first lumen 306' corresponding to the portion of the inserting section 305'.

That is, the arrangement is as follows. As shown in FIG. 41, if the inserting section 305' of the endoscope is inserted in the first lumen 306' so that the forward-end surface of the inserting section 305' is set to a location facing toward the opening end of the first lumen 306', it is possible to oppose the curved outgoing opening of the nozzle 311 mounted on the opening of the second lumen 307 at the forward end thereof, to the observation window 323 at the forward-end surface of the first lumen 306' without adjustment or regulation. Thus, the fluid is supplied from a portion of the second lumen 307 adjacent to a hand, whereby the fluid can be blown against the observation window 323 which is opposed to the outgoing opening. In this modification, it is possible to maintain a positional relationship between the nozzle 311 and the observation window 323 always constant, making it possible to ensure that the endoscope is cleaned without adjustment or regulation.

Other advantages are similar to those of the fifteenth embodiment.

In connection with the above, the arrangement may be such that, in, for example, the fifteenth embodiment, a tube having integrally mounted thereof the nozzle 311 is used in insertion into the second lumen 307 of the catheter 301 serving as a guide tube, and, after use, only the tube having integrally mounted thereon the nozzle 311 is discarded.

An example in which a cleaning tube for supplying fluid is separately provided in this manner will be described below.

Figure 42:
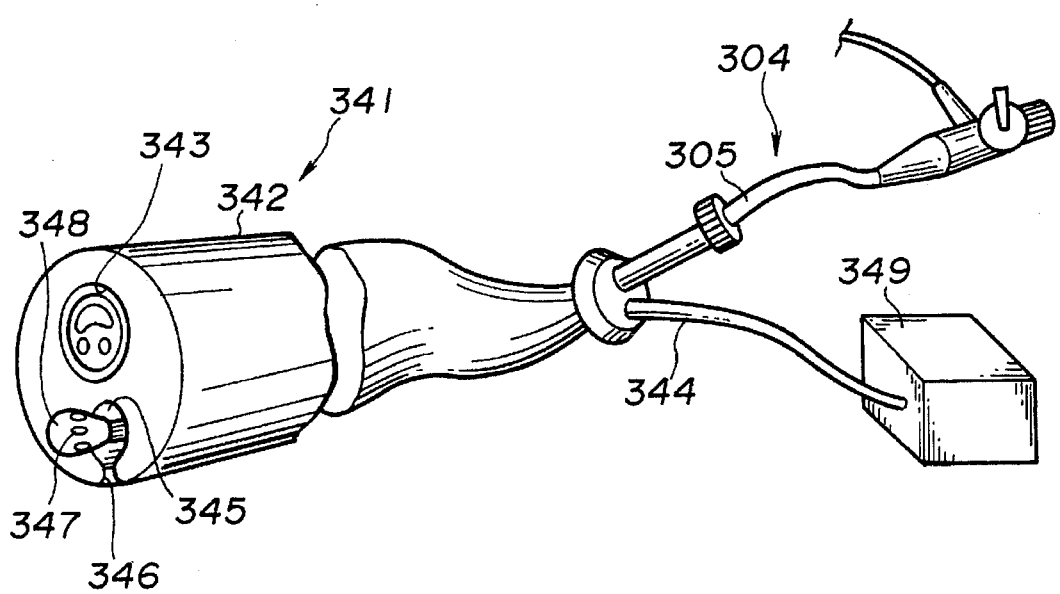
FIGS. 42, and 43(a) and 43(b) are views showing a sixteenth embodiment of the invention, FIG. 42 being a view for explanation, showing a condition under which an endoscope is inserted into a cleaning catheter.
Figure 43A:
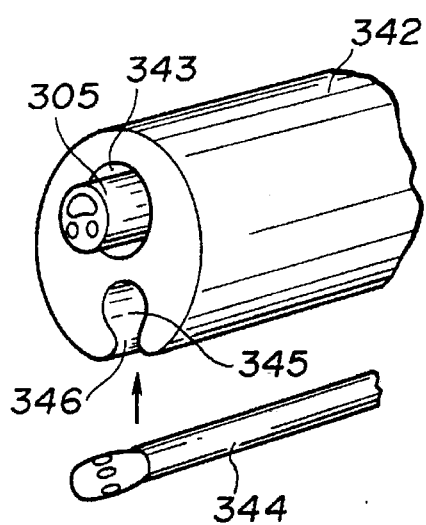
Figure 43B:
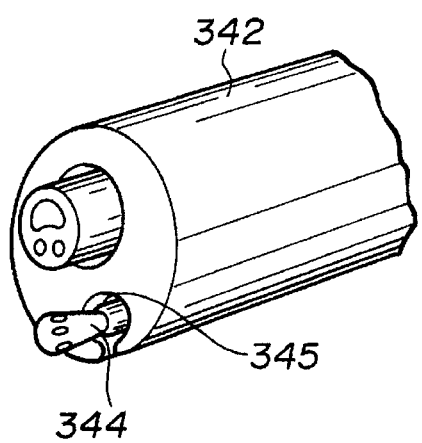

FIGS. 42, 43(a) and 43(b) show a sixteenth embodiment of the invention. FIG. 42 is a view for explanation, showing a condition under which an endoscope is inserted in a cleaning catheter, while FIG. 43 is a perspective view showing an arrangement of a forward-end portion of the cleaning tube.

As shown in FIG. 42, a cleaning catheter 341 according to the sixteenth embodiment has an elongated catheter portion 342 which is provided therein with a first lumen 343 in which an inserting section 305 of an endoscope 304 is insertable, and a second lumen 345 in which a cleaning tube 344 for leading cleaning fluid is insertable. The second lumen 345 is arranged such that the second lumen 345 is provided with a slotting portion 346 which faces toward an outer peripheral portion. By the slotting portion 346, the cleaning tube 344 can detachably be mounted laterally.

The forward-end tip 348 provided therein with the plurality of outgoing openings 347 is connected to the forward-end portion of the cleaning tube 344. A gas-feeding and liquid-feeding unit 349 is connected to a proximal-end portion of the cleaning tube 344. The arrangement is such that the cleaning fluid is introduced into the cleaning tube 344 so as to be capable of being outgone from the outgoing openings 347 at the forward end.

In the present embodiment, the inserting section 305 of the endoscope is inserted in the first lumen 343 and, as shown in FIG. 43(a), the cleaning tube 344 is mounted laterally from the slotting portion 346 so that the cleaning tube 344 is inserted into the second lumen 345 as shown in FIG. 43(b). By doing so, a line is formed which supplies fluid for cleaning the observation window of the endoscope 304.

In case where the forward-end portion of the endoscope 304 is cleaned, liquid or gas for cleaning is fed by the gas-feeding and liquid-feeding unit 349, and is led to the forward-end tip 348 through the cleaning tube 344. The cleaning fluid is outgone toward the forward-end portion of the endoscope 304 from the outgoing opening 347, so that extraneous matters adhered to the observation window and the like are removed.

In this manner, even by the arrangement in which the detachable cleaning tube is provided, it is possible to similarly clean the forward-end portion of the endoscope, and it is also possible to ensure that the endoscope is treated in disinfection. Moreover, it is possible to easily mount and demount the cleaning tube, and it is also possible to ensure that the cleaning tube is disinfected, and the like. Further, since the slotting portion is provided in the lumen on which the cleaning tube is mounted, it is possible to easily clean and disinfect the lumen.

Figure 44A:
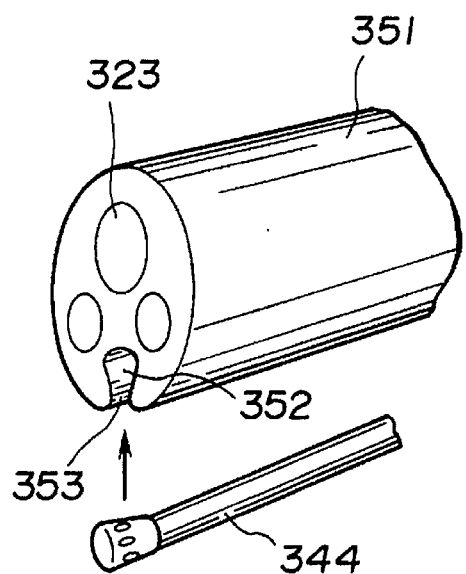
FIGS. 44(a) and 44(b) are vies for explanation, showing a forward-end portion of a cleaning tube apparatus according to a modification of the sixteenth embodiment.
Figure 44B:
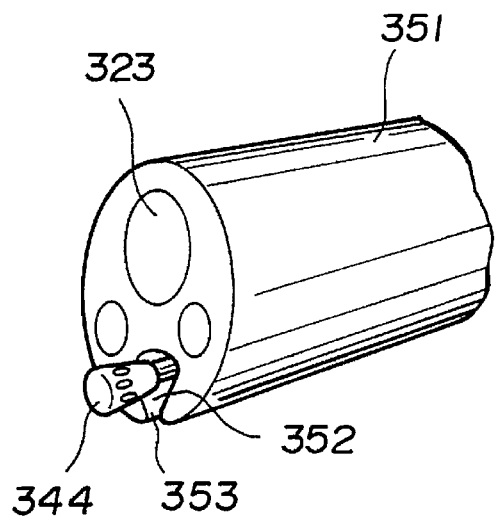

In connection with the above, as a modification of the sixteenth embodiment, as shown in FIGS. 44(a) and 44(b), the arrangement may be such that a lumen 352 is provided on an inserting section 351 of an endoscope. The lumen 352 is arranged such that a slotting portion 353 is provided which faces toward the outer peripherally similarly to the sixteenth embodiment. Thus, it is possible to detachably insert a cleaning tube 344.

When the endoscope according to this modification is used, as shown in FIG. 44(a), the cleaning tube 344 is mounted laterally of the slotting portion 353 so as to be inserted in the lumen 352, as shown in FIG. 44(b). Similarly to the sixteenth embodiment, the cleaning fluid is outgone from the outgoing opening of the cleaning tube 344 toward an observation window 323 in the inserting section 351 of the endoscope, and the like, whereby the forward-end portion is cleaned.

In this manner, the modification of the sixteenth embodiment has the advantages that, even in case where the lumen in which the cleaning tube is inserted is provided in the endoscope, it is possible to clean the forward-end portion of the endoscope, and it is possible to ensure disinfection treatment of various parts and the like, similarly to the sixteenth embodiment. Further, since the modification is arranged such that the cleaning tube is directly mounted on the inserting section of the endoscope, it is possible to reduce the diameter of the inserting section. Thus, it is possible to reduce or mitigate pain with respect to a patent at the use of the endoscope.

Figure 45A:
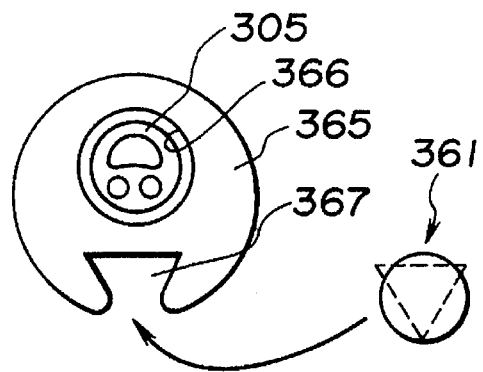
FIGS. 45(a) and 45(b) are views for explanation, showing a forward-end portion of a cleaning tube apparatus according to a seventeenth embodiment of the invention.
Figure 45B:
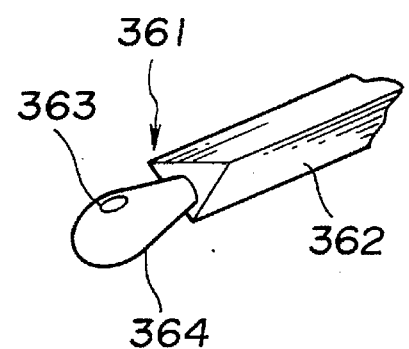

FIGS. 45(a) and 45(b) are views for explanation, showing a forward-end portion of a cleaning tube apparatus according to a seventeenth embodiment of the invention.

In the cleaning tube apparatus according to the seventeenth embodiment of the invention, as shown in FIG. 45(b), a cleaning tube 361 for leading cleaning fluid is formed with a triangular heteromorphic portion 362, and a forward-end tip 364 having, at a forward-end portion thereof, an outgoing opening 363 is connected to the cleaning tube 361. On the other hand, as shown in FIG. 45(a), an elongated catheter portion 365 is provided with a first lumen 366 in which an inserting section 305 of the endoscope 304 is insertable, and a second lumen 367 having such a heteromorphic configuration that the heteromorphic portion 362 is fitted in the second lumen 367. In this connection, the outgoing opening 363 in the forward-end portion 364 is so formed as to be directed toward the forward-end portion of the endoscope 304 inserted into the first lumen, under a condition that the cleaning tube 361 is mounted on the second lumen 367. Others are arranged similarly to the sixteenth embodiment.

In the present embodiment, the heteromorphic portion 362 of the cleaning tube 361 is so mounted as to be fitted in the second lumen 367 laterally. Similarly to the sixteenth embodiment, the cleaning fluid is led to the forward-end tip 364 through the cleaning tube 361, and is outgone toward the forward-end portion of the endoscope 304 from the outgoing window 363. At this time, the heteromorphic portion 362 and the second lumen 367 fitted in the heteromorphic portion 362 are formed into the triangular configuration. The cleaning tube 361 is not rotated within the second lumen, and the opening 363 is always oriented or directed toward the forward-end portion of the endoscope 304, so that the cleaning fluid is outgone.

In this manner, the cleaning tube and the lumen in which the cleaning tube is inserted are brought to heteromorphy, whereby it is possible to prevent the cleaning tube from being rotated within the catheter so that it is possible to always oppose the outgoing opening to the forward-end portion of the endoscope. Accordingly, it is possible to ensure that the observation window and the like of the endoscope are cleaned. Other function and advantages are similar to those of the sixteenth embodiment.

Figure 46:
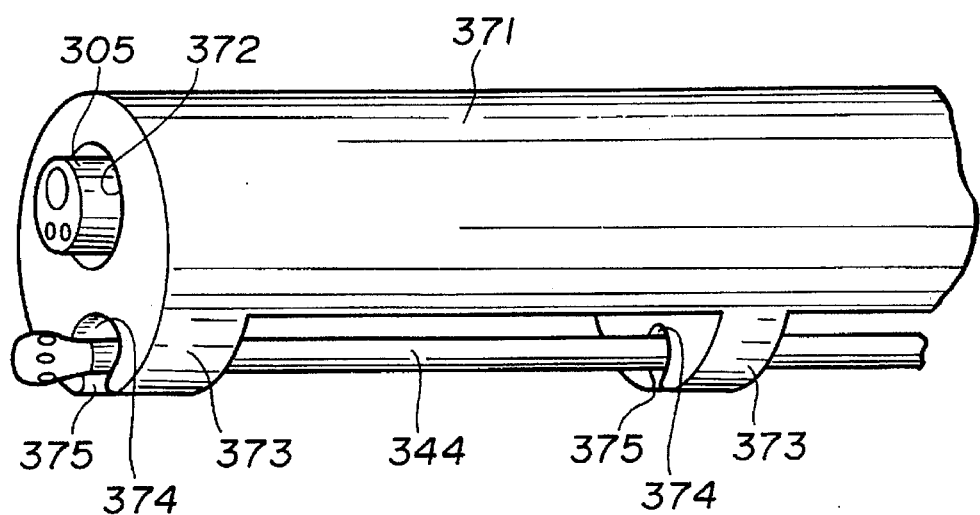
FIG. 46 is a perspective view showing a forward-end portion of a cleaning tube apparatus according to an eighteenth embodiment of the invention.

FIG. 46 is a perspective view showing a forward-end portion of a cleaning tube apparatus according to an eighteenth embodiment of the invention.

In the cleaning tube apparatus according to the eighteenth embodiment, an elongated catheter portion 371 is formed therein with a first lumen 372 in which an inserting section 305 of the endoscope is insertable. The elongated catheter portion 371 is provided with a plurality of projections 373 at predetermined intervals on a side surface portion of the elongated catheter portion 371. The projections 373 are provided with a second lumen 374 extending in parallel relation to the first lumen 372. A slotting portion 375 is formed in an outer peripherally of the endoscope. Each of the projections 373 is formed with a tube mounting portion on which a cleaning tube 344 can be mounted. Others are arranged similarly to the sixteenth embodiment.

When the cleaning tube apparatus according to the present embodiment is used, the inserting section 305 of the endoscope is inserted into the first lumen 372, while a cleaning tube 344 is mounted on the projections 373 laterally from the slotting portion 375, and is inserted into the second lumen 374. In case where the forward-end portion of the endoscope is cleaned, similarly to the sixteenth embodiment, the cleaning fluid is led by the cleaning tube 344, and the fluid is outgone toward the forward-end portion of the endoscope from the outgoing opening at the forward-end portion.

In this manner, even in case where the second lumen in which the cleaning tube is inserted is provided intermittently, there are produced advantages similar to those of the sixteenth embodiment. It is possible to further easily mount and demount the cleaning tube, so that operability can be improved.

Figure 47:
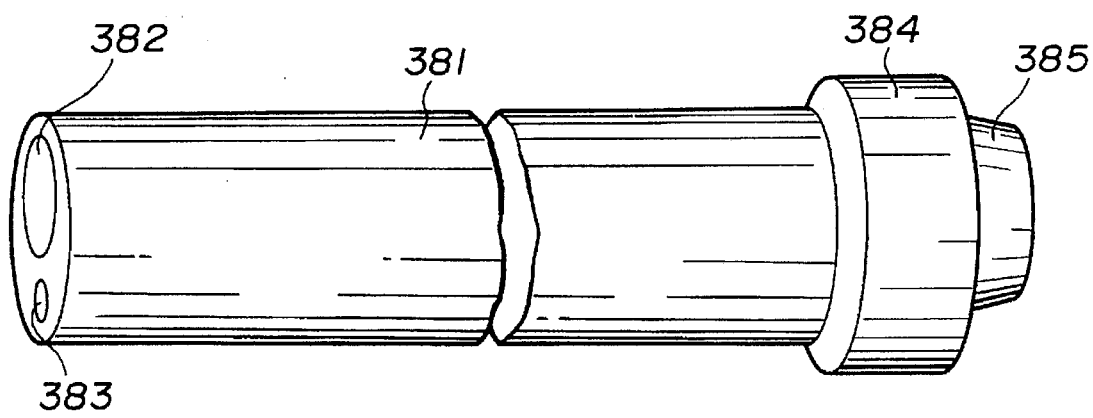
FIGS. 47 and 48 are views showing a nineteenth embodiment of the invention, FIG. 47 being a perspective view showing an arrangement of a cleaning tube apparatus.
Figure 48:
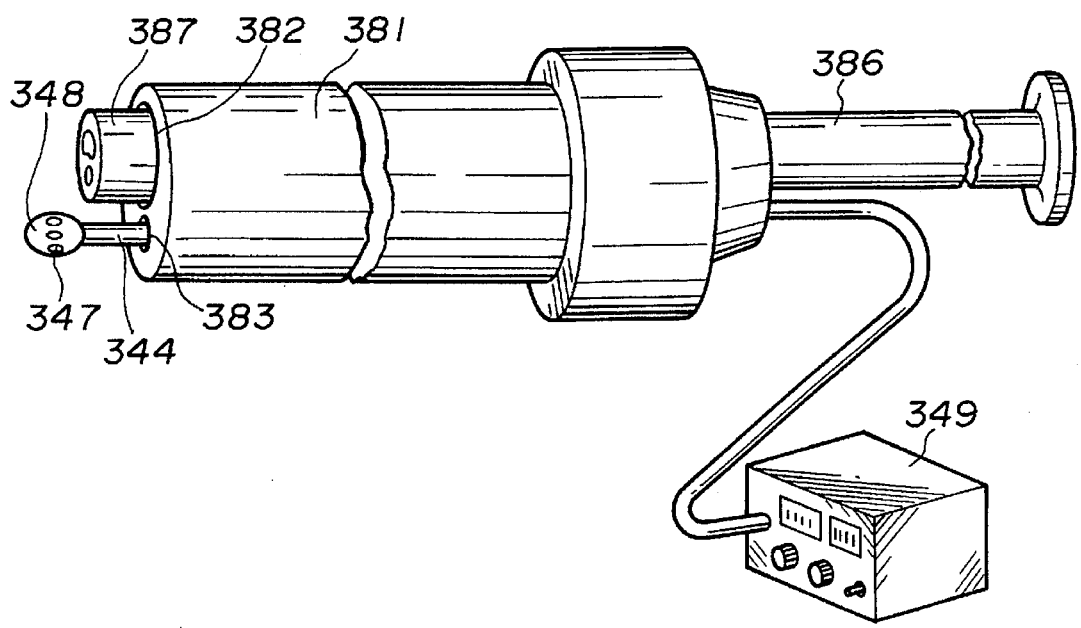

FIGS. 47 and 48 show a nineteenth embodiment of the invention. FIG. 47 is a perspective view showing an arrangement of a cleaning tube apparatus, while FIG. 48 is a view for explanation, showing a condition under which an endoscope is inserted.

The nineteenth embodiment is an example which is formed by a hard tube 381. The tube 381 is provided therein with a first lumen 382 in which the inserting portion of the endoscope is insertable, and a second lumen 383 in which the cleaning tube is insertable. The tube 381 has a proximal end thereof to which a holding portion 384 is connected. Further, at a hand, a seal element 385 is provided which prevents gas from leaking from the first and second lumens 382 and 383.

In the present embodiment, as shown in FIG. 48, an inserting section 387 of a hard endoscope 386, for example, is inserted in the first lumen 382, and a cleaning tube 344 similar to that of the sixteenth embodiment is inserted in the second lumen 383. A gas-feeding and liquid-feeding unit 349 is connected to the cleaning tube 344, to supply cleaning gas and liquid to the cleaning tube 344. The cleaning fluid is outgone from a plurality of outgoing openings 347 in a forward-end tip 348 through the cleaning tube 344, toward the forward-end portion of the inserting section 387, so that an observation window and the like of the endoscope 386 are cleaned.

In this manner, even in case where the cleaning tube apparatus is formed by the hard tube, it is possible to clean the forward-end portion of the endoscope, similarly to the sixteenth embodiment, and it is possible to easily mount and demount the endoscope and the cleaning tube. Thus, it is possible to ensure that various parts such as the endoscope, the cleaning tube and the like are treated in disinfection.

Figure 49:
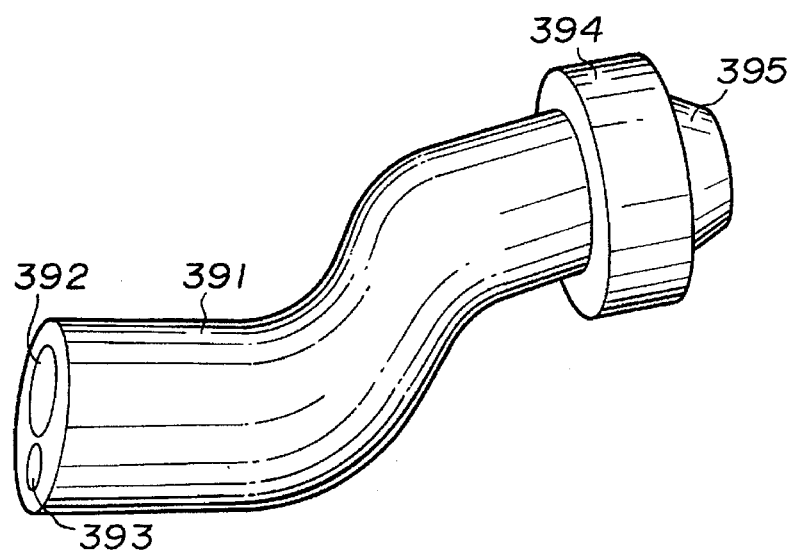
FIG. 49 is a view for explanation, showing an arrangement of a cleaning tube apparatus according to a twentieth embodiment of the invention.

FIG. 49 is a view for explanation, showing an arrangement of a cleaning tube apparatus according to a twentieth embodiment of the invention.

The twentieth embodiment is an example in which the cleaning tube apparatus is formed by a flexible tube 391 having flexibility, in place of the hard tube of the nineteenth embodiment. The flexible tube 391 has a first lumen 392 and a second lumen 393, similarly to the nineteenth embodiment. A holding portion 394 and a seal element 395 for maintaining gas tightness of various lumens are provided at a proximal-end portion.

That is, the twentieth embodiment is similar in arrangement to the nineteenth embodiment, except that the flexible tube 391 has flexibility. Even in case where the cleaning tube apparatus is formed by the tube having flexibility, there are produced function and advantages similar to those of the nineteenth embodiment.

It will be apparent in the invention that other various embodiments and modifications different from each other in a broad scope are formed on the basis of the invention, without departure of a spirit and scope of the invention. The invention should not be limited or restricted by specific embodiments and modifications of the invention, except that the invention is limited by the appended claims.

What is claimed is:

1. A cleaning tube apparatus in combination with an endoscope comprising:

an observation optical system for observing a subject part, said observation optical system including a plurality of objective lenses at a forward-end portion;

a cleaning tube detachable with respect to said endoscope, said cleaning tube being provided at one end with a plurality of fluid jetting openings each oriented in a rearward peripheral direction of said cleaning tube toward one of said plurality of objective lenses; and fluid supply means connected to said cleaning tube, for supplying the cleaning fluid to said cleaning tube.

2. A cleaning tube apparatus in combination with an endoscope comprising:

an observation optical system for observing a subject part, said observation optical system including a plurality of objective lenses at a forward-end portion;

a cleaning tube insertable in a channel in said endoscope, said cleaning tube being provided at one end with a plurality of fluid jetting openings each oriented in a rearward peripheral direction at one end of said cleaning tube toward one of said plurality of objective lenses; and fluid supply means connected to said cleaning tube, for supplying the cleaning fluid to said cleaning tube.

3. A cleaning tube apparatus in combination with an endoscope, according to claim 1, wherein said fluid supply means includes liquid feeding means for feeding the cleaning liquid to said cleaning tube.

4. A cleaning tube apparatus in combination with an endoscope according to claim 3, wherein said fluid supply means further includes gas feeding means connected to said cleaning tube for feeding gas to said cleaning tube.

5. A cleaning tube apparatus in combination with an endoscope, according to claim 1, wherein said fluid supply means includes liquid feeding means connected to said cleaning tube for feeding the cleaning liquid to said cleaning tube, and suction means connected to said cleaning tube for sucking the cleaning liquid from said fluid jetting openings in said cleaning tube.

6. A cleaning tube apparatus in combination with an endoscope, according to claim 5, wherein said liquid feeding means and said suction means are contained in a single liquid-feeding suction unit.

7. A cleaning tube apparatus in combination with an endoscope, according to claim 5, wherein said liquid feeding means and said suction means are provided by respective units separate from each other.

8. A cleaning tube apparatus in combination with an endoscope, according to claim 5, wherein said fluid supply means is provided with a reversible pump having a shaft which rotates in one direction to supply the cleaning liquid to said cleaning tube, and which rotates in an opposite direction to suck the cleaning liquid from said cleaning tube.

9. A cleaning tube apparatus in combination with an endoscope, according to claim 5, wherein said fluid supply means is provided with liquid-feeding suction control means for feeding the cleaning liquid for a predetermined period of time, and for sucking the cleaning liquid for a predetermined period of time after completion of liquid feeding.

10. A cleaning tube apparatus in combination with an endoscope, according to claim 5, wherein said fluid supply means is provided with a cleaning indicating switch for indicating cleaning operation; and liquid-feeding suction control means for feeding the cleaning liquid for a period of time said cleaning indicating switch is operated, and for stopping liquid feeding when operation of said switch is completed, to suck the clearing liquid for a predetermined period of time.

* * * * *